United States Patent
Brothers

(12) 
(10) Patent No.: US 6,372,493 B1
(45) Date of Patent: Apr. 16, 2002

(54) HORMONE-SECRETING CELLS MAINTAINED IN LONG-TERM CULTURE

(75) Inventor: Ann Janice Brothers, Fairfax, CA (US)

(73) Assignee: Pacific Biomedical Research, Inc. [Cell Mart, Inc.], Reno, NV (US)

( * ) Notice: Subject to any disclaimer, the term of this patent is extended or adjusted under 35 U.S.C. 154(b) by 0 days.

(21) Appl. No.: 09/301,110

(22) Filed: Apr. 28, 1999

Related U.S. Application Data

(63) Continuation of application No. 08/475,969, filed on Jun. 7, 1995, now Pat. No. 5,928,942, which is a continuation-in-part of application No. 08/167,862, filed as application No. PCT/US92/05267 on Jun. 23, 1992, now abandoned, which is a continuation-in-part of application No. 07/719,977, filed on Jun. 24, 1991.

(51) Int. Cl.⁷ .............................. C12N 5/00; C12N 5/02; C12N 5/08

(52) U.S. Cl. ...................... 435/384; 435/366; 435/375; 435/387; 435/388; 435/389

(58) Field of Search ................................ 435/325, 366, 435/375, 384, 387–389

(56) References Cited

U.S. PATENT DOCUMENTS

| | | | |
|---|---|---|---|
| 3,882,233 A | * | 5/1975 | Grant et al. .................. 514/21 |
| 4,288,546 A | * | 9/1981 | Narasimhan et al. ....... 435/70.3 |

OTHER PUBLICATIONS

Goodyer et al. J. Clin. Endocrinol. Metabolism. vol. 45, No. 1, pp. 73–85, 1977.*

Lipson et al. Acta Endocrinol. vol. 90, No. 3, pp. 421–433, 1979.*

* cited by examiner

Primary Examiner—Christopher R. Tate
(74) Attorney, Agent, or Firm—Karen S. Smith; Flehr Hohbach Test; Albritton & Herbert LLP

(57) ABSTRACT

Methods are provided for the establishment and maintenance in long term culture of hormone secreting cells. Cells are derived from tumorous or non-tumorous animal or human tissues, including ovary, endometrium, trophoblast, pituitary, thyroid, and pancreas. The cells secrete into the culture medium hormones such as estrogens, progestins, follicle-stimulating hormone, luteinizing hormone, human chorionic gonadotrophin, thyroxin, glucagon, and insulin, depending on the tissue of origin of individual cell cultures. Contact with an appropriate secretogogue causes the cells to respond with increased hormone secretion. For instance, ovarian follicular cells respond to follicle-stimulating hormone with increased estrogen and progesterone secretion. Pancreatic cells respond to elevated glucose with increased insulin secretion. The cells proliferate in in vitro for up to one year or longer, during which time they retain their hormone-secretion profile. The cells may be frozen for storage, and retain their hormone-secretion profile after thawing. The cell cultures are useful for the production of human hormones, for the bio-assay of drugs such as therapeutic gonadotrophin, for the testing of drug efficacy and design, and for toxicity testing of drugs and chemicals. The cells may also be implanted in an individual to replace deficient hormone secretion. For instance, insulin secreting pancreatic cells may be implanted in a diabetic individual as an adjunct or replacement therapy for exogenously administered insulin.

3 Claims, 5 Drawing Sheets

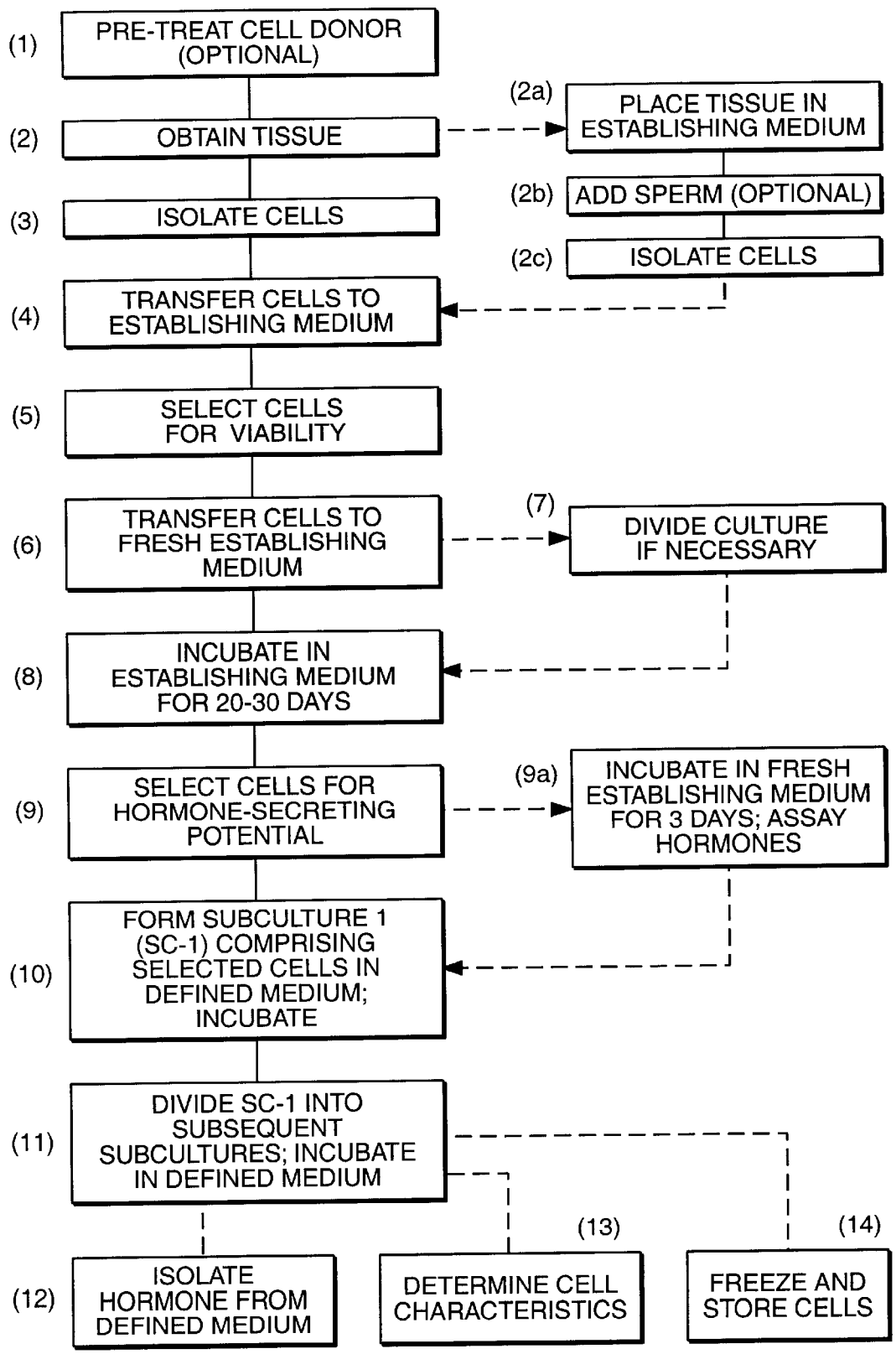
FIG._1

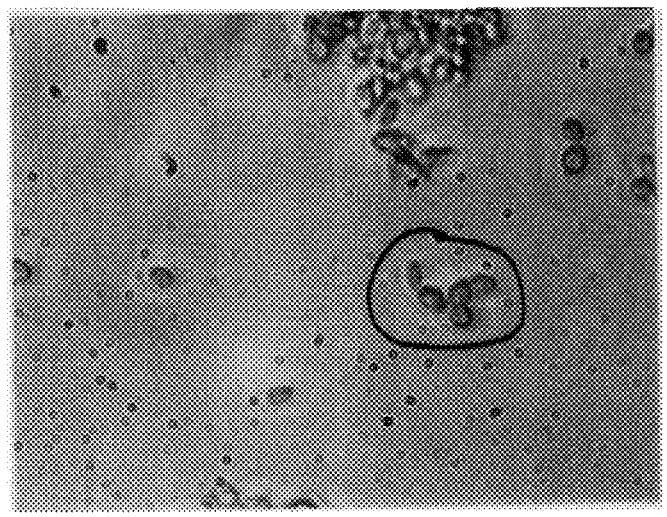
FIG._2
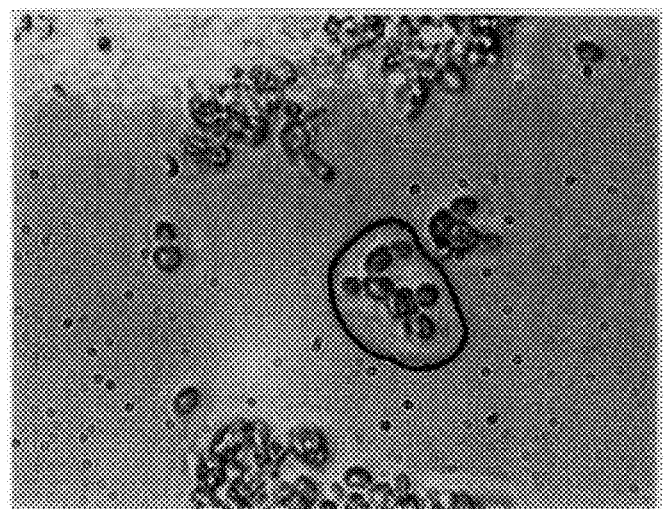
FIG._3
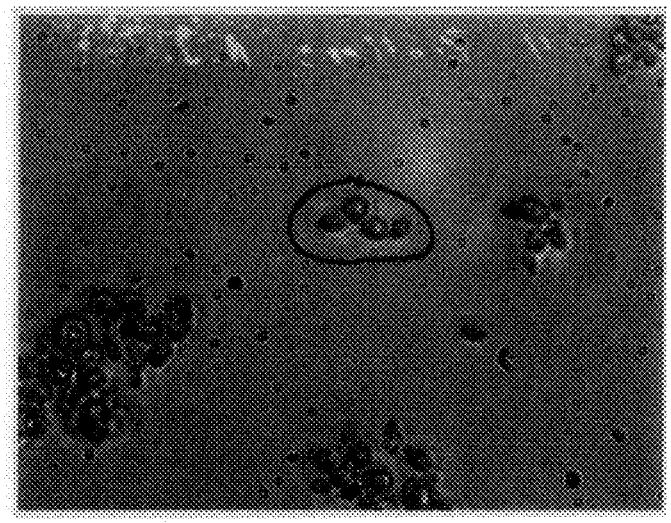
FIG._4

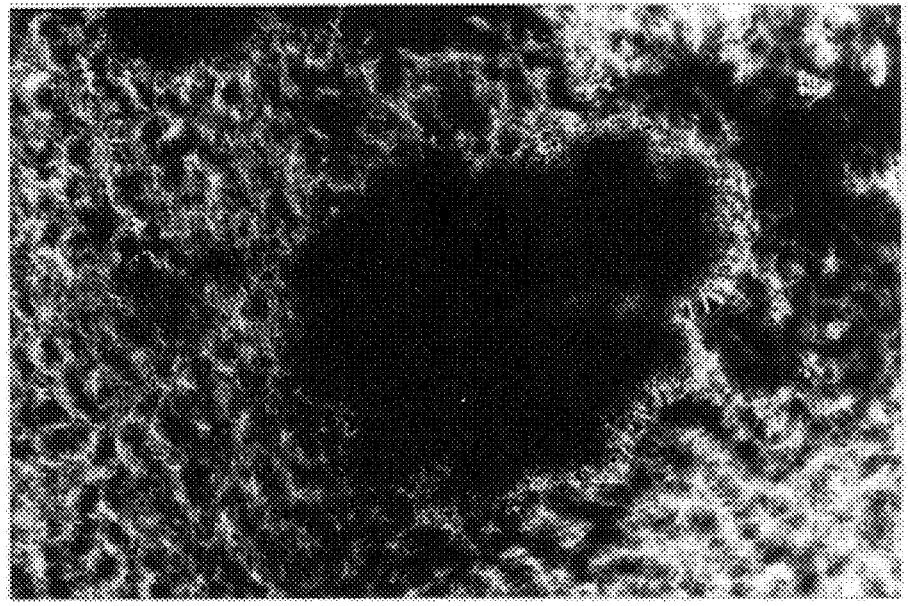
FIG._5
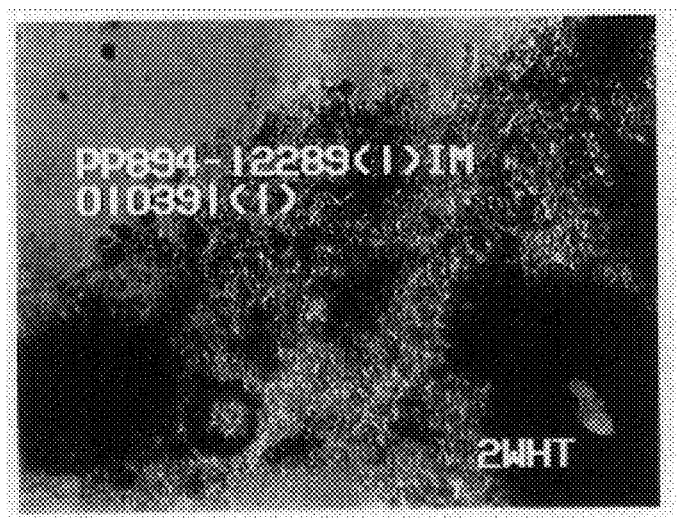
FIG._6
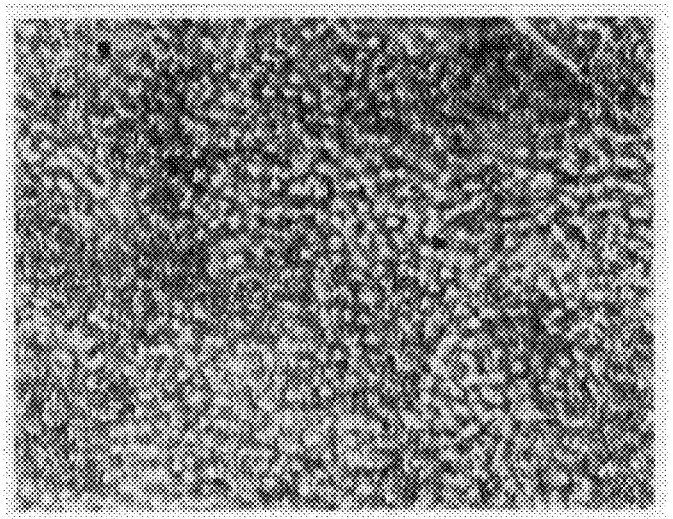
FIG._7

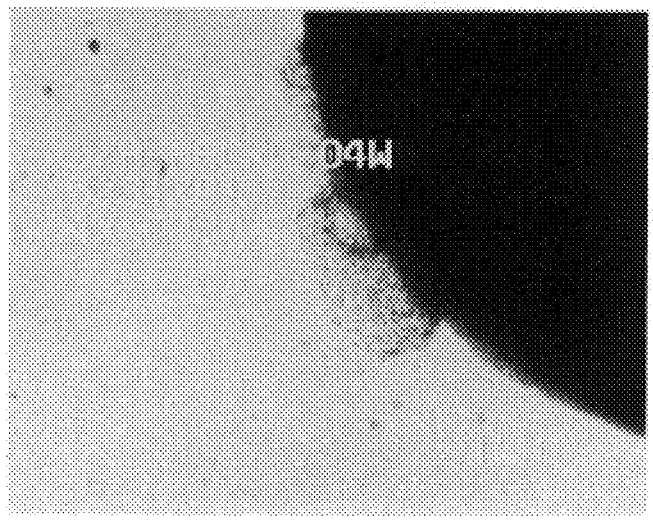
FIG._8
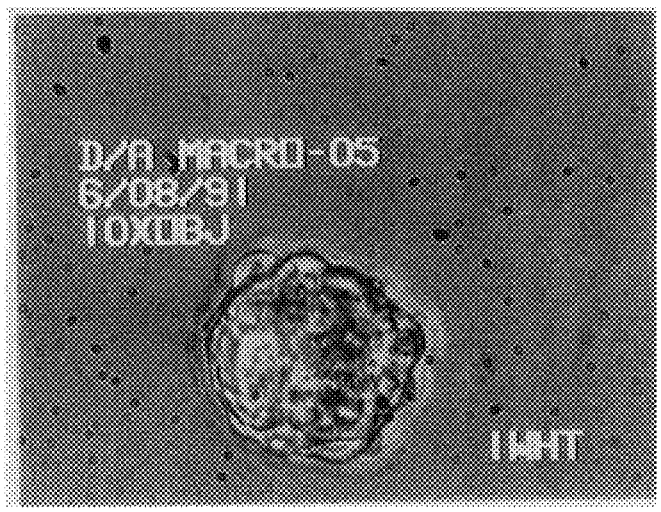
FIG._9
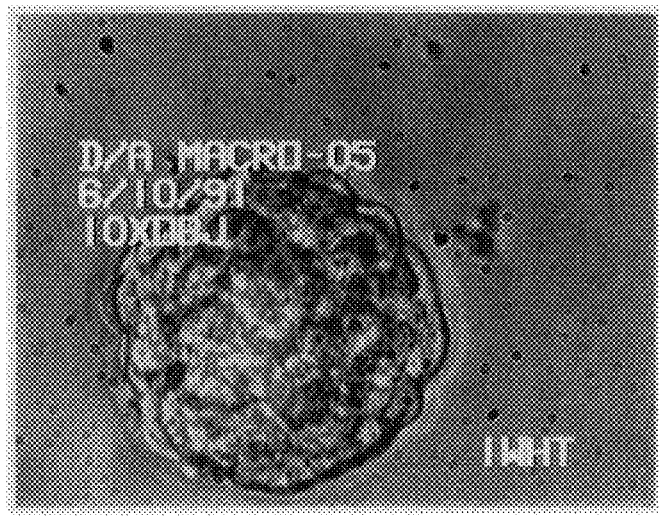
FIG._10

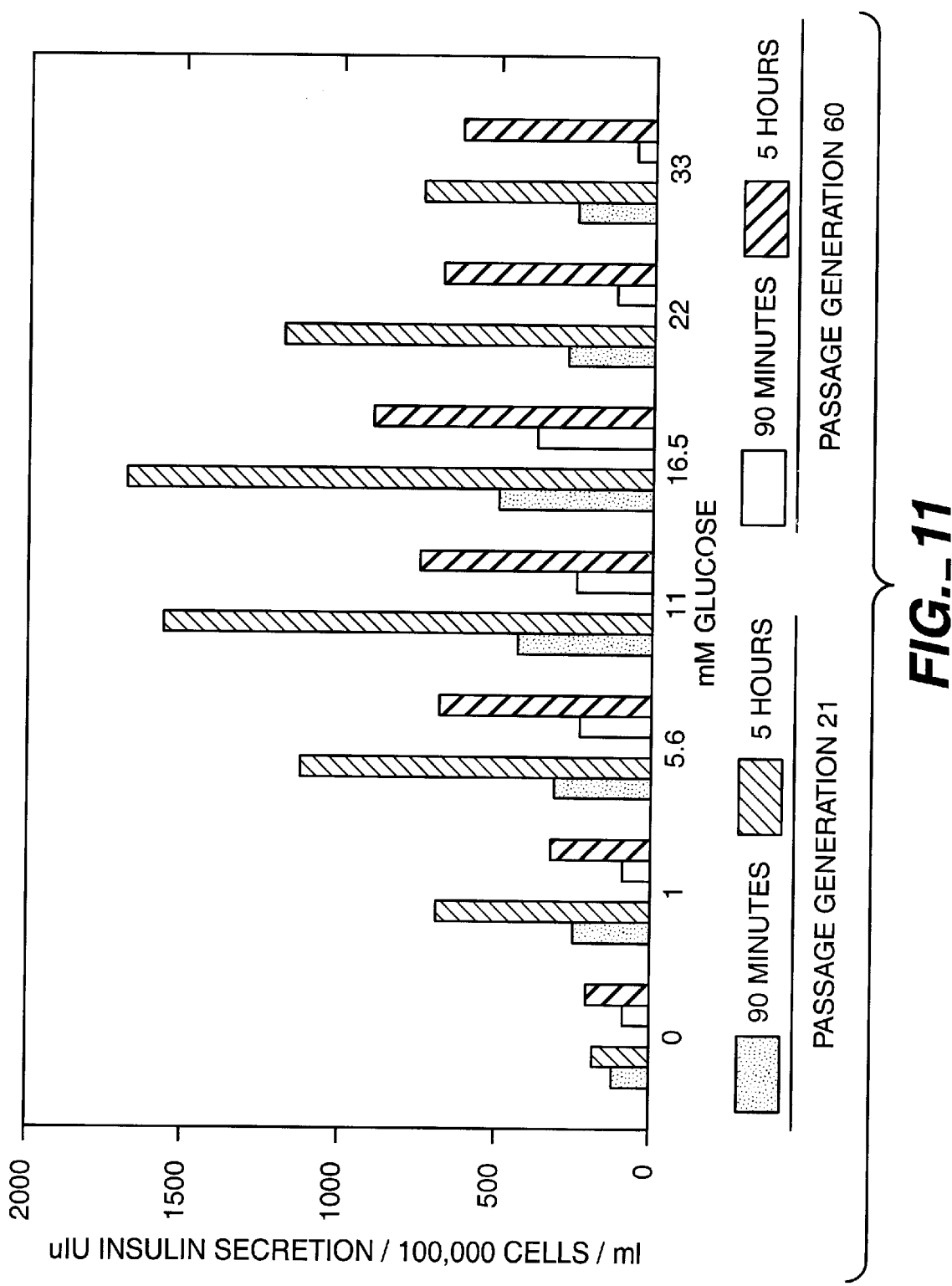
FIG._11

HORMONE-SECRETING CELLS MAINTAINED IN LONG-TERM CULTURE

CROSS-REFERENCE TO RELATED APPLICATION

This application is a continuation of U.S. patent application Ser. No. 08/475,969 filed Jun. 7, 1995, now U.S. Pat. No. 5,928,942, issued Jul. 27, 1999, which is a continuation-in-part of U.S. patent application Ser. No. 08/167,862, filed Apr. 29, 1994 (now abandoned), which is a 371 national stage entry of PCT/US92/05267, filed Jun. 23, 1992, entitled "Hormone-Secreting Cells Maintained in Long-Term Cultures" which is a continuation-in-part of U.S. patent application Ser. No. 07/719,977, filed Jun. 24, 1991, now abandoned, entitled "Hormone Secreting Cells Maintained in Long-Term Culture for the Production of Hormones, for Bio-Assay of Drugs, and for Toxicity Testing of Drugs and Chemicals". Related applications are Ser. No. 08/477,067, filed Jun. 7, 1995, now U.S. Pat. No. 5,821,121, issued Oct. 13, 1998, and Ser. No. 08/486,737, filed Jun. 7, 1995, now U.S. Pat. No. 5,787,341, issued May 5, 1998.

TECHNICAL FIELD

The invention relates to long-term proliferating in vitro cultures of hormone-secreting cells and to methods for establishing, maintaining, and propagating hormone-secreting cells in culture.

BACKGROUND ART

Hormone-secreting cells are highly differentiated and specialized for the synthesis and secretion of typically one or two specific hormones. Examples of hormone-secreting cells include certain cells of the pituitary gland, the endometrium, the ovary and the pancreas. The pituitary gland contains cells specialized for the synthesis and secretion of glycoprotein hormones known as gonadotrophins, follicle-stimulating hormone (FSH) and luteinizing hormone (LH), which act on the gonads. The gonadotrophins secreted by the pituitary enter the blood stream and reach the gonads, where they exert their affects. Within the ovary, upon stimulation with gonadotrophins, granulosa cells surrounding an ovum differentiate within the preovulatory follicle to synthesize and secrete estrogen and progesterone. Specialized cells of the endometrium also synthesize and secrete estrogen and progesterone. Within the pancreas, β-cells of the islets respond to increased blood glucose concentration with an increase in insulin secretion.

Conventional cell culture technology is sufficient for the propagation of certain cell types in vitro such as fibroblasts taken from normal tissue or from tumors. It has long been a goal of scientists to maintain hormone-secreting cells in vitro, however standard culture conditions do not promote the long-term survival or proliferation of hormone-secreting cells. For practical purposes, it would be desirable to establish in culture cells which both proliferate and perform their specialized functions, i.e., synthesis and secretion of specific hormones.

For primary tissue culture, normal or tumor cells are removed from an animal or a human cell donor, placed in a liquid chemical medium in laboratory culture dishes, and maintained in an incubator under physical conditions which mimic the cells' environment in vivo. The medium and the incubator environment provide regulated temperature, pH, nutrients, growth factors, protection against pathogens, and in some cases a necessary substrate for cell attachment. Even under optimized culture conditions, however, most types of normal cells have a limited life span in culture. Typically, when cells other than fibroblasts are established in primary tissue culture they do not proliferate; they may or may not continue to perform their differentiated functions over the short-term. When the cells reach the end of their natural life-span they die, thus the cultures are self-limiting. Hormone-secreting cells generally survive in culture for no more than 8 to 12 days, during which time they undergo few or no cycles of cell division. During the life-span of hormone-secreting cells in culture, as they have been maintained using prior known techniques, such cells typically undergo a loss of function as evidenced by a decrease in hormone production.

In order to increase the life-span of hormone-secreting cells in culture, published techniques have included the use of embryonic cells. The strategy of starting with embryonic cells is based on the fact that embryonic cells are relatively less differentiated than adult cells, and thus can be expected to go through several cycles of cell division before becoming terminally differentiated, i.e., specialized for hormone synthesis. It is an axiom of biology that undifferentiated cells proliferate at a greater rate than differentiated cells. It is generally believed that by the time a cell has developed the necessary intra-cellular machinery for hormone synthesis and secretion, it is no longer able to divide rapidly, if at all.

Another known strategy for establishing cells in culture is to start with cancer cells, since cancer cells would be expected to have a greater potential for proliferation. However, few cells derived from tumors or other cancerous lesions are able to become established and divide in culture. One cell line was established from a malignant human choriocarcinoma by propagating the tumor cells through 304 serial transplantations to the hamster cheek pouch over a period of 8 years before establishment in vitro (BeWo cell line; ATCC CCL 98; May 1990 supplement to the 1988 American Tissue Culture Collection [ATCC] catalog of cell lines). The BeWo cell line was reported to produce human chorionic gonadotrophin (hCG), polypeptide hormones, human placental lactogen (hPL), estrogens and progestins. A cell line with an abnormal karyotype was established from the malignant ascites of a patient with adenocarcinoma of the ovary (NIH:OVCAR-3; ATCC HTB 161; ref. supra). The OVCAR-3 cell line was reported to possess androgen and estrogen receptors, however no synthesis of hormones by these cells was reported.

A rat clonal beta-cell line (RIN) was established in culture from a rat insulinoma (Clark, S. A., et al, 1980, *Endocrinology* 127:2779–2788). RIN cells were reported to secrete insulin in vitro in response to low levels of glucose, with maximal response at 0.6 mM glucose. This response is comparable to that of immature rat beta-cells, and quite different from that of normal mature rat islets which secrete in response to glucose concentrations ranging from 5 mM to 16 mM.

It is apparent from the forgoing that tumor cells are difficult to establish in vitro. Moreover, tumor cells that do become established in culture often possess abnormal characteristics which diminish their usefulness, such as the loss or alteration of hormone synthesis or secretogogue responsiveness.

Using a strategy based on the notion that abnormal cells are more likely to grow in vitro, normal cells have been transformed in culture by various means including the use of UV light, chemical carcinogens, and the introduction of oncogenes. Rat granulosa cells were transformed by co-transfection with the entire SV 40 genome and the activated Ha-ras gene (Baum, G., et al. 1990 *Develop Biol* 112:115–128). These cells were reported to retain at least some differentiated characteristics, i.e., they were able to synthesize steroids in response to cAMP.

Other cell lines established in culture include UMR cells, derived from normal islets of neonatal rats (NG, K. W., et al., 1987, *J. Endocrinol.* 113:8–10) and HIT cells, derived by simian virus-40 infection of hamster islets (Santerre, R. F., et al., 1981, *PNAS* 78:4339–4343). The insulin secretory output of these cell lines is low, and response to glucose is lost with passage in culture.

In order to promote the selection of non-transformed hormone-secreting cells as starting material for culture, a regimen of hormone treatment in vivo was used before removal of cells from the donor (Amsterdam, A., et al. 1989 *Endocrinology* 124:1956–1964). Cells were obtained from ovarian follicles removed from women who had received hormonal therapy in preparation for in vitro fertilization. For additional promotion of differentiated function, cells were maintained on extra-cellular matrix and further treated with human chorionic gonadotrophin (hCG). Although the cells had a differentiated appearance and secreted progesterone in culture, the cells were reported to survive in culture for only five days. In a similar study, cells were reported to survive for eight days (Pellicer, A., et al. 1990 *Fertility and Sterility* 54:590–596).

Another strategy for promoting the maintenance of differentiation in culture involved the culturing of the component parts of entire follicles, including the oocyte and cumulus complex (Vanderhyden, B. C., et al. 1990 *Develop. Biol.* 140:307–317). In this type of "combination culture", mouse granulosa cells were maintained in a differentiated state for 7 days.

The above description of the state-of-the-art makes it apparent that there is a need for methods to maintain and propagate hormone-secreting cells in long-term cultures. Such cultures could be developed as biological "factories" for the production of therapeutically useful hormones. Well-established hormone-secreting cell lines would also offer the possibility of in vitro bio-assays based on the cells' responses to drugs such as gonadotrophin preparations. In addition, such cell lines would offer the possibility of in vitro bio-assays for the toxicity of drugs and other chemicals. Established cell lines would also be candidates for implantation to correct diseases due to hormone deficiencies. For instance, diabetics could be stabilized and possibly cured through the implantation of cells which replace the function of insulin-secreting beta-cells of the pancreas.

There exists a need for methods to produce consistent physiologically correct preparations of gonadotrophin hormones. Human gonadotrophin preparations (hMG), which typically contain both FSH and LH, are administered to women who are undergoing pre-treatment leading to in vitro fertilization. The administered hMG stimulates the woman's ovaries to produce multiple pre-ovulatory follicles, which are subsequently aspirated for in vitro fertilization. hMG is currently derived from the urine of post-menopausal women. Each lot differs according to the age and endocrine status of the urine donors, the differences being in both concentration and types of isoforms present in the final product. There are at least 11 isoforms of human follicle-stimulating hormone (hFSH) and 7 isoforms of human luteinizing hormone (hLH) (Stone, B. A., et al. 1990 *Acta Endo* (*Copenhagen*) 123:161–168). Analysis by high-performance liquid chromatography (HPLC) of various hMG preparations showed between-lot variability in the presence and concentration of isoforms of FSH (Stone, B. A. et al, supra). Different isoforms have different biopotencies (Gharib, S. D., et al. 1990 In: *Endocrine Reviews* 11:177–199). Since certain isoforms of FSH are more biopotent than others, there is between-lot variability in biopotency among various hMG preparations. Moreover, the presence of LH isoforms in a preparation affects the biopotency of FSH present in the preparation.

Scientists are currently attempting to produce genetically engineered FSH of a desired and consistent biopotency. There is a clear need for a cost-effective assay to enable the development of therapeutically useful preparations of genetically engineered gonadotrophins.

There exist two major forms of chemical assay for gonadotrophins: HPLC and radioimmunoassay (RIA). The HPLC technique is precise but does not identify which chemical properties of hMG preparations relate to biopotency. Moreover, the HPLC technique requires considerable technical expertise, instrumentation, and investment of technical labor. Tests based on immunologic recognition of a gonadotrophin (RIA) are limited by the inherent cross-reactivity of the antibodies with disparate isoforms of the gonadotrophins. For instance, a single RIA numerical value for FSH concentration could include several FSH isoforms of differing biopotency. Thus the current techniques for chemical assay do not provide a means to assess the biopotency of a therapeutic preparation of gonadotrophin.

The need for biopotency assessments of gonadotrophins has been acknowledged by several national agencies, including the U. S. Food and Drug Administration (FDA). The assays currently accepted by the FDA are in vivo assays conducted in rodents. The in vivo assay for FSH is the Steelman-Pohley assay which is based on mouse uterine weight gain. One in vivo assay for LH is the rat Leydig cell assay; the degree of proliferation in the seminal vesicles of the immature male rat is the index for assessing biopotency of LH. Another in vivo bioassay for LH is the rat ovarian ascorbic acid depletion test. These in vivo assays are disadvantageous because they require the sacrifice of large numbers of laboratory animals. For instance, the sacrifice of 2,000 mice is required to measure the stability factor for one particular batch of hMG. This figure of 2,000 mice does not include the number required to establish the biopotency of the original batch. The need for a more cost-effective bioassay is apparent. Moreover, the results from tests conducted on rodent cells are not necessarily applicable to biopotency in humans.

The current source for therapeutic gonadotrophins, while convenient, is limited by the inherent biological variability among the human donors. The major source of human gonadotrophin (human menopausal gonadotrophin, hMG) is urine donated by members of a religious order in Switzerland. The post-menopausal women living within the convent pool their urine for sale to a company which derives each lot of its product from a batch of the pooled urine. Since the age and endocrine status of each donor to the urine pool changes from batch to batch, each preparation of gonadotrophin is different in chemical composition and in biopotency. Thus there exists a need for a consistent source of human gonadotrophin.

There also exists a need for a source of physiologically correct preparations of human sex steroid hormones. Currently, therapeutic estrogen and progesterone compounds, and analogs thereof, are prepared by standardized chemical synthesis. However, the class of compounds designated "estrogens" produced normally in the human female includes several different formulae and isoforms. Similarly, the class of hormones designated "progestins" includes several different compounds and isoforms. The types and amounts of estrogens and progestins produced naturally vary according to the female's age and overall physiological status, i.e., the specific time point in her menstrual cycle, pregnancy, or menopause. The optimal steroid content for any given therapeutic indication has not been determined. Even if the optimal chemical profile of a sex steroid preparation were determined, chemical synthesis would not be a practical route for production of complex steroid mixtures. Therefore, it is desirable to develop methods which inherently provide a physiologically correct mix of human estrogens and progesterones.

Toxicity testing is another field which scientists have attempted to address through use of in vitro systems (for review see: Nau, H. 1990. in *Methods in Developmental Toxicology: Use in Defining Mechanisms and Risk Parameters*. Eds. G. L. Kimmel, D. M. Kochhar, CRC Press, pp. 29–43.) To date, in vitro systems based on hormone-secreting cells have been very limited, partly because of the difficulties inherent in maintaining hormone-secreting cells in culture. In theory, the reproductive toxicity of a compound could be assessed by the capacity of the compound to impair hormone-secretion from cells which characteristically secrete a given hormone. A non-human cell line (Chinese hamster ovary, CHO) has been extensively utilized for toxicology analyses, (Tsushimoto, G., et al., 1983 *Arch Environ Contam Toxicol* 12:721). Amphibian oocytes have been proposed as a system for the testing of tumor promoting compounds (U.S. Pat. No. 4,983,527; issued Jan. 8, 1991). Xenopus testis explants have been proposed for the testing of mutagenicity and genotoxicity during spermatogenesis (U.S. Pat. No. 4,929,542; issued May 29, 1990). Cell lines established from rat embryo fibroblasts have been proposed as systems for screening for protein inhibitors and activators (U.S. Pat. No. 4,980,281; issued Dec. 25, 1990). Since it is generally recognized that humans have different toxic susceptibilities compared to amphibians and rodents, the above proposed in vitro testing systems are limited by the non-human origins of the cells.

Thus, there exists a need for human hormone-secreting cell lines established in long-term culture for the purposes of 1) production of human hormones, 2) bio-assay of therapeutic gonadotrophins, 3) testing of drug efficacy and design, 4) toxicity testing of drugs and chemicals, and 5) implantation to replace deficient hormone secretion.

DISCLOSURE

This invention provides methods for establishing hormone-secreting cells in vitro and for maintaining the viability of at least a portion of the cells in an establishing culture medium for at least about 13 days.

This invention also provides methods for the long-term maintenance and propagation in defined media of hormone-secreting cells in vitro.

According to this invention, cells may be obtained from animal or human donors of normal or tumorous tissues from ovary, trophoblast, endometrium, pituitary, pancreas, or thyroid. In vitro, the cells secrete hormones characteristic of their tissue or tumor of origin. Examples of secreted hormones include estrogens, progestins, gonadotrophins (LH, FSH, hCG), insulin, glucagon, and thyroxin. Cells may respond to stimulation by secretogogues with increased hormone secretion. In particular, cells of ovarian origin may respond to stimulation by gonadotrophins with increased secretion of progesterone and/or estrogen.

It is an object of this invention to provide methods for the production of established hormone-secreting cell lines which may be cryopreserved and propagated from frozen stock, and which retain a characteristic hormone-secretion profile over several generations in vitro.

It is an object of this invention to provide a method for the production of therapeutically useful hormones by propagating hormone-secreting cells in culture and isolating the secreted hormones from the culture medium surrounding the cells.

It is a further object of this invention to provide hormone-secreting cells in culture suitable for an in vitro bio-assay for the biopotency of therapeutic hormone preparations.

It is an additional object of this invention to provide an in vitro toxicology assay based on changes in hormone secretion by human cells in vitro in response to contact by the chemical agent being tested.

It is a further object of this invention to provide cells maintained in long-term culture useful for implantation in a subject to replace deficient hormone secretion.

BRIEF DESCRIPTION OF THE DRAWINGS

FIG. 1 is an outline of the general method for establishing and propagating hormone-secreting cells in vitro.

FIG. 2 is a photomicrograph (4900×total magnification) of a typical culture of human ovarian follicular cells after the completion of step 8 in FIG. 1.

FIG. 3 provides a second example of the cells depicted in FIG. 2.

FIG. 4 provides a third example of the cells depicted in FIG. 2.

FIG. 5 is a photomicrograph (approximate final magnification=560×) of a typical culture of follicular cells after one week in subculture (see Example 2).

FIG. 6 is a photomicrograph of a typical initial sub-culture of follicular cells (SC-1; see Example 2).

FIG. 7 is a photomicrograph (2500×approximate total magnification) of a typical sub-culture of follicular cells after more than 20 rounds of serial sub-culture (see Example 2). The cells were seeded four days previously at a density of $10^6$ cells per 15 ml medium in a 25 cm$^2$ flask.

FIG. 8 is a photomicrograph (1100×approximate total magnification) of a "blastema-like" outgrowth of cells at the edge of a section of original pituitary macroadenoma which had been placed in culture 9 days previously.

FIG. 9 is a photomicrograph (2200×total magnification) of a group of cells which detached from an outgrowing "blastema-like" projection after the original piece of pituitary adenoma had been in culture for 18 days.

FIG. 10 is another photomicrograph taken two days later of the same group of cells as in FIG. 9 (20 days total culture time for the original tumor section). The magnification is the same as in FIG. 9, thus illustrating by comparison the rapid proliferation of these cells.

FIG. 11 is a histogram depicting increased insulin secretion by human pancreas cells in response to increased glucose concentration.

BEST MODE OF CARRYING OUT THE INVENTION

An outline of the general method of the invention is provided in FIG. 1; steps indicated below refer to FIG. 1.

Briefly, cells with hormone-secreting potential are carefully isolated from a surgical tissue sample according to methods provided herein. Preferably, cells to be established in culture are obtained from a human donor undergoing a medical procedure during which tissue is removed as a part of the procedure (step 2).

Unless otherwise noted, as used in the application, the terms "derived from", established from" or "originated from" or variations thereof, when used to define cellular status, mean a biological (mitotic) descendant status. That is to say for example that a cell or cells "derived from" a pancreatic islet or a pancreatic islet cell or cell entity (e.g., a nodule containing a cell or cells) are progeny of that islet, cell or the cell or cells in the cell entity.

Following tissue removal, the cells are gently isolated from the tissues (step 3) and initially established in culture under conditions which sufficiently mimic the in vivo environment so that the viability of the cells is promoted (steps 4–6). After approximately 30 days under establishing culture conditions (step 8), the cells are selected for hormone-secreting potential (step 9). Selected cells are placed into sub-cultures and further maintained and propagated in defined medium (steps 10 and 11). The defined medium is formulated to promote cell proliferation and the continued viability of the sub-cultures. Useful hormones may be isolated from the medium (step 12). After sufficient cells are propagated, the cell cultures are characterized for proliferation rate, secretion of hormones, and responses to secretogogues and toxins (step 13). Aliquots may be cryopreserved (step 14) and tested for retention of cell line characteristics. When a cell line is sufficiently characterized, it may be designated an established cell line and may be used for the production of hormones or for biopotency or toxicity assays.

In one embodiment of the invention, cells are obtained from ovarian follicles removed from a donor undergoing in vitro fertilization. At the time of follicular extraction, the donor has typically been treated with a combined hormonal regimen to stimulate the development of multiple pre-ovulatory follicles (step 1). The hormonal regimen typically includes leuprolide acetate for midluteal suppression combined with human menopausal hormone (hMG) and follicle-stimulating hormone (FSH) for controlled ovarian hyper-stimulation. Thirty-four hours prior to oocyte retrieval, human chorionic gonadotrophin (hCG) may be administered to promote further growth and differentiation of the follicle. The above described hormonal regimen stimulates the proliferation of the granulosa cells surrounding the ovum. Towards the end of the follicular growth phase, two populations of granulosa cells develop: 1) mural granulosa cells which maintain contact with the basal lamina enclosing the follicle, and 2) the cumulus granulosa cells, also known as zona radiata cells, closest to the ovum, which are coupled by gap junctions to both the oocyte and other surrounding cumulus cells. Gonadotrophin stimulation of granulosa cell differentiation is characterized by changes in cell-cell contacts, cell shape, cytoskeletal organization, and biosynthesis of estrogens, progesterone, progestins, extracellular matrix components, and hormone receptors. FSH acts by a cAMP mediated mechanism on undifferentiated granulosa cells to stimulate the enzymatic activity required for the metabolism of cholesterol to progesterone and-for the conversion of androgens to estrogens. As the follicle matures, FSH and estrogen stimulate the production of granulosa cell plasma membrane associated LH receptors. After FSH priming and the synthesis of LH-receptors, granulosa cells become responsive to LH and will then synthesize progesterone in response to added LH.

The above described hormonal treatment regimen thus favors the development of granulosa cells which exhibit a high level of basal progesterone and estrogen secretion. Such cells are desirable, for instance, for the production of therapeutic human sex steroids or for an in vitro toxicity assay based on reduction of hormone secretion by a toxic agent. When development of the follicles is optimal, the follicles are aspirated in preparation for in vitro fertilization of the ova. In this context "tissue" (step 2) refers to the entire follicle, including the basal lamina, cumulus granulosa cells, mural granulosa cells and ovum. Generally, non-germ line follicular cells accompany the extracted ova (step 2), and these non-germ line cells would usually be discarded during the normal course of the in vitro fertilization method. Cells are isolated for culture (step 3) from the follicles of those patients who donate their non-germ line cells for medical research and development for health care applications.

In contrast to the above described embodiment, follicular cells which exhibit low basal levels of hormone secretion, but which respond to gonadotrophin with increased hormone secretion, are desirable for in vitro biopotency assays for therapeutic gonadotrophin preparations. Therefore, in a second preferred embodiment, follicular cells are obtained from a donor who has undergone only the first part of the above described pretreatment regimen. The donor has received hMG and FSH but not hCG. In this embodiment, relatively undifferentiated follicular cells are obtained from growing primary follicles, rather than from mature pre-ovulatory follicles.

In a third preferred embodiment, follicular cells are obtained from a donor who has not undergone any pretreatment regimen. In this embodiment, relatively undifferentiated follicular cells are obtained from primary follicles, rather than from hormone-stimulated pre-ovulatory follicles. Similarly to the above described second embodiment, follicular cells obtained by this method exhibit low basal levels of hormone secretion while retaining the ability to respond to gonadotrophin with increased hormone secretion. Therefore, cells obtained by this third embodiment are likewise useful for in vitro gonadotrophin bio-potency assays.

Two important features which distinguish this invention method from conventional methods are (1) the tissue is not subjected to enzymatic digestion, except for the use of collegenase in conjunction with pancreatic islet cell isolation, and (2) the cells are not subjected to centrifugation. This contrasts with published methods which require digestion of the tissue matrix by incubation with enzymes such as hyaluronidase and trypsin in order to release cells from the tissue matrix. After enzyme treatment, conventional methods typically rely on centrifugation to isolate cells from the resulting debris. Herein, the term "substantially enzyme free" refers to a process in which enzymes are not added to the incubation medium. It is understood that small amounts of enzymes such as proteases may be present in any medium, and the presence thereof is allowed within the definition of the term "substantially enzyme-free".

The first step after obtaining the follicular cells is to place cells, with or without the ovum, in an establishing medium (EM; step 4). The term "establishing medium" refers to a solution which essentially mimics the critical parameters of the in vivo environment from which the cells were derived. Five specific formulations for establishing media are disclosed herein. Critical parameters of the in vivo environment of follicular cells include an osmolarity which is reduced compared to the osmolarity typically used in previous attempts to culture hormone-secreting cells. The osmolarity of follicular fluid is generally in the range of 270 to 275 mOsm. Thus the final osmolarity of an establishing culture medium of the present invention ranges preferably from about 248 mOsm to about 300 mOsm, more preferably from about 260 mOsm to about 280 mOsm, most preferably from about 270 mOsm to about 275 mOsm.

It is preferred to flood the cells in the establishing medium with a medical blood gas mixture composed of 5% $CO_2$/5% $O_2$/90% $N_2$, which mimics the gas mixture in vivo. It is also preferred to supplement the establishing medium with extra glutamine, to a value of about 6.35 mM to about 8.35 mM, most preferably 7.35 mM glutamine.

In one preferred embodiment of the invention, the establishing medium is supplemented with serum obtained from the specific cell donor (establishing medium, homologous serum; EMHS). Preferably, the EMHS contains 0.5% to 15% homologous serum, more preferably 5% to 10% homologous serum, most preferably 7% to 8% homologous serum. The use of homologous serum provides an environment which contains no proteins other than those proteins which are specific to the individual from whom the cells were derived, and thus favors the viability of the donated cells because of the minimization of immunologic reaction. Additionally, donor serum may be favorable for its specific content and concentration of hormones such as progesterones, estrogens, and gonadotrophins.

In another embodiment of the invention, the establishing medium is supplemented with serum obtained from an individual other than the specific cell donor (establishing medium, non-homologous serum; EMNS). Preferably, the EMNS contains 0.5% to 15% non-homologous serum, more preferably 5% to 10% non-homologous serum, most preferably 7% to 8% non-homologous serum. It will be apparent to those skilled in the art that medium may also be variously supplemented with hormones and growth factors to promote the survival of cells with desired characteristics, such as elevated progesterone production.

In a further embodiment of the invention, cells are successfully established in a defined medium which does not contain serum, but rather is supplemented with bovine serum albumin (BSA) or a combination of BSA and purchased serum substitute. The term "defined medium" refers to a culture medium which does not contain human serum, and thus contains fewer unknown, unassayed components than does human serum-containing medium. It is understood that medium which contains any animal-derived product, such as BSA, is not as completely defined as a medium which is composed entirely of chemically synthesized components. However, in the art of the present invention, BSA-containing media and serum-substitute containing media are commonly referred to as "defined media". In the present application, the generic term "defined medium" refers to any medium which does not contain human serum. Provided in the experimental examples to follow are formulae for six different defined media: 1) establishing medium-01 (EM-01); 2) defined medium-1 (DM-1); 3) defined medium, serum substitute (DMSS); 4) OCZEM-M (Formula V); 5) modified RPM1-1640 (Formula IV plus fetal calf serum and zinc) and 6) RPMI-1640 glucose deficient medium (Formula VI). These six defined media share the characteristic of containing, instead of human serum, BSA and/or a serum substitute containing animal proteins and/or some human proteins.

Herein, the term "serum substitute" refers to a combination of proteins and growth factors, preferably added in the amount of about 5% to about 15% of the total volume of the medium. EM-01 was originally devised to promote the viability of fertilized ova from a donor whose serum contained anti-sperm antibody. Fortuitously, the substitution of BSA for donor serum also promoted the viability of non-germ line follicular cells which were cultured at the same time as the ova. Therefore, EM-01 is a preferred establishing medium for follicular cells. The media designated DM-1 and DMSS were originally formulated for use after 30 days in EM containing human serum (EMHS and EMNS). However, it was found that cells may be successfully established in DM-1 or in DMSS without being previously placed in EM containing human serum. Formula V, OCZEM-M medium, is the preferred medium for pancreas islet cells. EM-01, DM-1, DMSS and Formula V share the distinguishing characteristics of EM containing human serum in that they also have a lower osmolarity than do conventional culture media. The osmolarity of EM-01, DM-1 and DMSS is preferably in the range of about 248 mOsm to about 300 mOsm, more preferably in the range of about 260 mOsm to about 280 mOsm, most preferably about 270 mOsm to about 275 mOsm. The osmolarity of Formula V is preferably in the range of 245 mOsm to about 300 mOsm, more preferably in the range of 255 mOsm to about 280 mOsm, most preferably about 260 mOsm to about 268 mOsm.

Suitably, the media formulations employed in this method may contain, in addition to glucose, additional energy sources such as lactate and pyruvate. The term "energy source" refers to a chemical which can be used by the cells to make ATP either through glycolysis or through the tricarboxylic acid cycle.

As with establishing medium, it is preferred to supplement defined media formulations with added glutamine to the amount of about 6.35 mM to about 8.35 mM, most preferably about 7.35 mM glutamine.

Suitably, the ovum and surrounding non-germ line follicular cells are placed together in EM (EMHS, EMNS, EM-01, DM-1, DMSS; step 2a). After about 24 hours, sperm may be added to the EM, and the cells may be incubated for an additional 20–24 hours (step 2b). It is generally believed that spermatozoa provide an enzyme known as acrosomal enzyme, which gently releases the non-germ line cells from the matrix surrounding the ovum. Within the context of the present invention it is understood that the amount of spermatozoa-associated acrosomal enzyme is small and is not comparable to the large amounts of enzymes such as collagenase which are employed in traditional methods for digesting tissue matrices to release cells. After incubation in sperm, cells of the corona radiata may be manually stripped from the ovum through use of a hollow needle as described in Example 1 (step 2c). Suitably, follicular cells which do not adhere to the ovum may be simply isolated from the surrounding medium (step 3).

Viable cells are selected through a dissecting microscope (90×magnification; step 5). The term "viable" refers to cells which typically show monolayer spreading on the bottom of a culture dish. Viability may be confirmed in a dispensable sample of cells by the method of trypan blue dye exclusion as is well known in the art of the present invention. The method of the present invention is again distinguished in step 5, as well as in step 3 supra, from the methods of Amsterdam, et al (supra) and Pellicer, et al (supra) in that no centrifugation or gradient separation is used in the present technique. Instead, cells are manually and gently selected and isolated for culture, which preserves the membrane integrity of a larger number of cells as compared with cell populations that have undergone centrifugation. The method of the present invention is again distinguished from techniques which require enzymatic digestion of tissue to isolate cells. Such well known techniques typically involve incubation in trypsin or collagenase, which may be injurious to the cells desired for the practice of this invention.

Selected cells are placed in fresh EM with the aid of a fine glass micropipette and incubated for a further 24 to 96 hours (step 6). It is preferred to flood the cells with the medical blood gas mixture described supra to best mimic gas conditions in vivo. At this point, cells may be divided into cultures containing 50 to 100 cells in fresh EM (step 7).

The selected cells are further maintained in the establishing medium for up to about 30 days (step 8). During the first 14 days, culture medium is refreshed only every 6 to 7 days. This produces a slight hypoxia of the cultures and is a physiological selection against fibroblasts, since rapidly dividing cells such as fibroblasts do not survive in a lowered $O_2$ atmosphere (Aladjem, S. et al. 1981 *Placenta Suppl.* 3:175). The lowered $O_2$ atmosphere is concomitantly a positive selection for cells of granulosa origin since their normal in vivo milieu is of a similar condition.

Commonly, in some initial cultures, a high proportion of the cells are able to survive and proliferate without attachment to a substrate. In contrast, a number of the cells spread on the bottom of the culture plate and form attachments to the plastic. Thus a given cell culture may comprise both cell clumps floating in suspension, cell clumps adhering to the plastic dish, and cells spreading in monolayer fashion on the bottom of the dish.

After about 20 to 30 days in the establishing in vitro environment (step 8), cells are chosen for hormone-secreting potential (step 9) according to morphological criteria as depicted in FIGS. 2, 3, and 4. The circled clumps of cells are representative of the type of cell clumps that are selected. Preferably, small clumps of 2 to 12 cells are chosen, most preferably clumps of 4 to 5 cells. Selected clumps are combined into groups of 50–150 cells (step 9a) or alternatively into groups of 10–15 cells (step 10). These groups are designated first sub-cultures (SC-1). Because of the spatial arrangement of cells within a selected clump, i.e., touching each other in a "string-of-pearls" type arrangement, it is thought that these clumps have a high probability of containing daughter cells arising from the division of 1 or 2 progenitor cells. It is often desired to obtain a clonally selected culture arising from the progeny of a single cell, and thus these clumps have a high probability of providing such a culture when a single clump is used for SC-1 (e.g., step 10 in which a single clump of 10–12 cells forms the starting culture). FIG. 6 shows a typical initial sub-culture of follicular cells in SC-1. The dark spots are particularly dense clumps of cells in which individual cells were not photographically resolvable. The lighter colored cell layers in between the dark spots are cells which spread on the bottom of the culture plate and on which the camera was focused. (The white lettering on the photo is merely a record-keeping designation and does not contain information for this patent application.)

It will be apparent to one skilled in the art that the possibility exists for clonal selection at any point in the subsequent subculturing procedures (step 11).

Criteria for cells with hormone-secreting potential include an approximately spheroid or ovoid shape, and homogeneity of size and shape within a clump, as illustrated by the circled clumps in FIGS. 2, 3, and 4. These selection criteria are based on the Applicant's observations of follicular cells, and specifically of granulosa cells, using phase contrast optics and microsurgical manipulations, and on the study of histological preparations and scanning electron micrographs of follicular cells. It will be apparent to one of skill in the art of the present invention that the above described and depicted selection criteria are to be understood in the context of comparison to other, non-selected cells in the field of view (FIGS. 2, 3, and 4). Thus the selected cell clumps contain fewer cells than the non-selected clumps, and the individual cells are more homogeneous than cells of the non-selected clumps. Selected cells have a smooth-appearing plasma membrane, in contrast to non-selected cells which typically have plasma membranes with ruffled leading edges. Also, in the case of follicular cells, the cytoplasm of selected cells typically appears smooth rather than granular.

Methods for removing cells to subcultures (steps 10 and 11): In the case of cells which are growing on and attached to the bottom of the culture plate, cells are harvested for sub-culture by gently scraping the cells from the plate with the aid of a fine glass micropipette. This method contrasts with methods which use enzymatic or other harsh methods such as calcium chelation to detach cells from substrate. Of course, in the case of cells which are growing in suspension, no detachment step is necessary.

Selected cells are transferred to a defined medium (steps 10 and 11, e.g., DM-1, DMSS, described supra). The defined medium formulations described herein allow the cells to proliferate and to maintain hormone secretion capability. The culture flasks or plates containing cells and medium are flooded with the medical blood gas mixture described supra and kept sealed within a 37° C. incubator. Preferably, the cells proliferate in culture over a long term of at least about 2 months, more preferably at least 5.5 months, most preferably longer than 15 months. The cell cultures are typically flooded with medical blood gas mixture every other day and subdivided as needed according to the density of the proliferating cell population.

In certain embodiments of the invention, the defined medium has a higher initial pH than that typically used in previous attempts to culture follicular cells. The pH values of the media designated DM-1 and DMSS are initially adjusted to 7.65, in contrast to the conventional culture medium pH of 7.4. The rationale for using a higher initial pH is based on the fact that follicular fluid and granulosa cells exist in vivo in a slightly elevated $CO_2$ environment and mammalian embryos have a higher pH when compared to maternal serum (Nau, H. et al 1986 *Nature* 323:276–279; Nau, H. 1990 supra). The higher initial pH of the establishing medium of the present invention may protect the cells from damage by weak acids by minimizing the production of same. It will be apparent to one skilled in the art of the present invention that there are various alternative techniques which could control the effects of weak acids. Therefore, the initial pH of 7.65 is offered only as an enabling suggestion, and is not to be construed as a limitation on the methods of the present invention. Moreover, the establishing media designated EMHS, EMNS, and EM-01 have pH values ranging from 7.2 to 7.45, thus a more conventional pH is sufficient to establish hormone-secreting cells in culture, and may also be sufficient to propagate such cells in culture.

During the first six days in the first sub-culture (step 10), cell number typically increases about 2-fold, preferably about 3-fold or greater. During the later part of the first sub-culture, and during subsequent sub-cultures, cell proliferation rate increases to a doubling time of preferably about 72 hours, more preferably about 48 to 36 hours or less. FIG. 6 shows the typical appearance of an initial sub-culture after 14 days in culture (step 10). In FIG. 6 the dark spots are large cell clumps comprising 200 cells or greater; the lighter colored cell areas between the clumps are layers composed of single cells or a few cells spreading on the bottom of the culture dish.

FIG. 7 is a photomicrograph of follicular cells after more than 20 sub-cultures (step 11) which were plated at a density of $10^6$ cells/15 ml/25 cm$^2$ four days previous to the photographic date. In FIG. 7 the camera lens is focused on only the lower layer of cells closest to the bottom of the culture dish, and there are many layers of floating clumps of cells between the medium surface and the lowest cell layer. Thus, the typical cell density of a culture similar to that depicted in FIG. 7 is preferably about $3 \times 10^6$ to about $4 \times 10^6$ cells/15 ml/25 cm$^2$.

After a period of proliferation, upon reaching a saturating cell density, an individual culture may exhibit slowed or halted proliferation. In one embodiment of the invention, such a "dormant" culture may be useful when differentiated characteristics, such as responses to secretogogues, are preserved. A dormant culture may be useful for the bio-assay of gonadotrophin potency as described below. Alternatively, a proliferating culture may also be used in a gonadotrophin bio-assay.

In another embodiment of the invention, by repeated serial sub-culture, a large population of like cells is obtained (step 11). Suitably, portions of the population are frozen in a cryoprotective medium and are stored in liquid nitrogen (step 14). Protocols for freezing cells, as described in Example 15, represent traditional techniques as well as more complex techniques which are currently used for the freezing of embryos. Because of the large size of certain hormone-secreting cells in culture, particularly pituitary cells (FIGS. 8–10; Example 13), it is suitable to employ freezing techniques which are designed for use with embryos, which are of a comparably large size. However, simple and conventional techniques may be employed when a smaller viability percentage is considered acceptable. Upon thawing, the cells may exhibit the characteristic proliferation and hormone-secretion patterns of the population from which they were derived. In a preferred embodiment, a cell population is propagated and cryopreserved to provide an essentially unlimited supply of cells having defined characteristics. Such a characterized and stored population is known as an "established cell line".

During the time in establishing medium (step 8) and during the time in sub-culture (steps 10 and 11), the cells are capable of secreting at least one human hormone. In a preferred embodiment of the invention, the cells secrete estrogens and/or progestins, of a typically human isomeric composition, at rates sufficient for the isolation of the hormone(s).

In another embodiment of the invention, the cells of a specific population do not secrete a high basal level of steroid hormone. The cells do, however, respond to stimulation by gonadotrophins with detectably increased steroid hormone secretion. Preferably, a maximum dose of FSH, for instance, stimulates a 2–20 fold increase, more preferably a 4–10 fold increase, most preferably a 5–8 fold increase in the amount of steroid hormone secreted into the medium over a period of from 24 to 48 hours. Preferably, the increase in steroid secretion may be correlated with the dose and type of gonadotrophin administered to the cells, thus defining the hormone secretion profile of the population. The term "hormone-secretion profile" refers to (1) the specific secretogogues to which the cells respond, (2) the type(s) of hormone(s) and (3) the amounts of hormones which are secreted in response to a specified secretogogue. Established cell lines may be employed as bio-assays for gonadotrophin bio-potency.

In a further embodiment of the invention, cells are derived from human trophoblastic tissue most preferably tissue of non-tumorous origin. The cells are established in culture and sub-cultured as described above and illustrated in Example 12. Trophoblastic cells preferably secrete hCG and other hormones. Populations of cells of non-tumorous trophoblastic origin are suitably employed in bio-assays of potential reproductive toxins. The bio-assays are based on the reduction or alteration of basal sex hormone secretion upon contacting the cells with a potential toxin.

In another embodiment of the invention, cells are derived from human endometrium. The endometrial cells are established in culture and sub-cultured according to any of the above described methods. The populations of endometrial cells in culture preferably secrete high levels of progestins and/or estrogens such that they can be used as sources for therapeutically useful hormone preparations. Suitably, the endometrial cell populations are also used in bio-assays for reproductive toxicity.

In a preferred embodiment of the invention, cells are isolated from a human pituitary tumor. The cells may be established and propagated in culture by any of the above described methods and as illustrated in Example 13. Suitably, the tumor tissue is initially sectioned into pieces of approximately 1–3 mm diameter and individual pieces are placed in establishing medium for 15 to 20 days. During this time, outgrowths of cells develop and separate from the original piece of tumor (FIGS. 8–10 ). The cell outgrowths are referred to as "blastema-like", an embryological term for a cell group which gives rise to an organ. The separated "blastema" cell groups are then transferred into individual cultures for further propagation in defined medium. Preferably, the pituitary cells secrete at least one human gonadotrophin such as FSH or LH. Suitably, human FSH or LH is isolated from the medium surrounding the cell cultures to form a therapeutically useful gonadotrophin preparation.

In other embodiments of the invention, cells are obtained from tumors or normal tissue of the thyroid or pancreas and propagated in vitro according to methods described herein. Suitably, to establish thyroid or pancreatic cells in culture, a variation of the establishment method is used. The tissue may be placed directly in establishing medium, then the tissue is teased into small chunks through use of a sterile scalpel. Preferably, the chunks contain about 50 to 300 cells.

The chunks are aliquoted into several dishes and flooded with the medical blood gas mixture described supra. They are kept in sealed containers for about two weeks, and the gas is refreshed every other day. The cells proliferate during this time. After two weeks, the cell cultures may be subdivided and maintained for approximately 8 additional weeks in establishing medium. The cultures may be subdivided as needed during this time, depending on how quickly the cultures proliferate. It will be apparent to one skilled in the art that the possibility exists for clonal selection at any point in the subculturing process. The medium of each culture is assayed for hormone content. Suitably, cells derived from thyroid tissue secrete thyroxin and cells derived from pancreas secrete insulin. Cultures containing a desired level of hormone are selected for further culture in defined medium (FIG. 1, step 10). Suitably, when suspension culture is desired, cells may be selected which did not adhere to the surfaces of the culture vessels but rather are floating suspended in the medium.

Pancreas cells treated accordingly have been maintained in long-term continuous culture for as long as four years. Portions of the pancreas cell cultures are frozen at intervals according to the methods described in Example 17. When these frozen cultures are thawed and placed in defined medium, the cells retain their ability to synthesize and secrete insulin.

In yet still another embodiment human pancreas whole islets may be obtained from sources such as biopsies or human organ donor cadavers (brain dead) and isolated by commonly used collagenase digestion methods to yield pancreas whole islets comprised of islet cells enclosed in a basement lamina. These isolated whole islets may be placed in a large volume of "transport medium", such as RPMI-1640 (sigma) in a test tube or culture flask such as "NUNCLON", polystyrene resin, (Seco, Rolling Hills, Pa.) or "FALCON" (Becton Dickinson, Franklin Lakes, N.J.) and transported to other destinations at temperatures ranging from 4° C. to room-temp overnight or for less than 24 hrs. Upon receipt the whole islets are placed into culture dishes containing room temperature defined medium, preferably OCZEM-M described in Example 22. The preferred number of whole islets is from about 15–20 per dish but as little as one whole islet may be separately cultured. NUNCLON culture dishes were used but other dishes are also acceptable. The culture dishes are placed into a sealed glass container (desiccator) and gassed with a medical blood gas mixture (5% $O_2$, 5% $CO_2$, 90% Nitrogen—certified). The container is placed in a 37° C. incubator for 4–6 hrs and allowed to slowly warm. The islets are then transferred to fresh defined medium so that preferably 3 to 5 whole islets per 7–8 cc defined medium are in each NUNCLON culture dish. Again the culture dishes are placed into the sealed glass containers and regassed with the medical blood gas mixture. The whole islets are allowed to equilibrate for 24 hours.

The basement lamina surrounding the whole islet is then gently ruptured manually or mechanically. As used herein "gentle" rupture of a membrane or lamina means piercing the membrane but leaving the membrane sufficiently intact so that the already developed cells present inside the membrane do not exit and become separated from the membrane and whole islet of origin at the time of rupture. The rupturing can be done by any deliberate mechanical or manual method, provided the method is sufficiently gentle. The preferred method of rupture is by microsurgery. Microsurgery using sterile glass microneedles causes a tiny breach in the basement lamina surrounding the islet. This approximates the series of events that occur during pancreas development, where destabilization of a small area of the constricting basement lamina elicits subsequent islet cell proliferation and growth of the islet (Beerfield, M. et al. (1982), "The Turnover of Basal Lamina Glycosaminoglycen Correlates with Epithelial Morphogenesis", *Div. Biol.* 90:291–305; Rutter, W. J. et al. (1978), "An Analysis of Pancreatic Development: Role of Mesenchymal Factor and Other Extracellular Factors", J. Papaconstantineu and W. J. Rutter, eds., *Molecular Control of Proliferation and Differentiation,* Academic Press, New York, pp. 205–227, and Wessells, N. K. (1977), *Tissue Interaction and Development,* W. A. Benjamin, Menlo Park, Calif.). The microsurgically constructed breach provides an opening in the basement lamina so that a few islet cells are gently extruded in an attached tiny nodule. This tiny nodule will remain attached to the large whole islet during the subsequent days or even weeks of culture. Cell proliferation occurs within and at the periphery of the tiny nodule so that it increases in size. Eventually the larger nodule will break off forming a "daughter-islet" containing one or more cells. Another series of islet cells will extrude through the hole in the basement lamina of the large whole islet to form another tiny nodule and the series of events will repeat. The independent daughter-islet will remain suspended in the culture medium or very loosely attached to any fibroblasts which might be tightly adhered to the bottom of the culture dish. These small daughter-islets may be transferred to new culture dishes giving sub-cultures of islet cells. The doubling time for these islet cells is about 3–10 days, resulting in a 20-fold increase in cell number by four months of culture. In general the media is changed about every 2–3 days and the cells are passed about every 10 days. These daughter-islet cells did not adhere tightly to the bottom of the culture dish, but remain independent or very loosely adherent. Cells derived from daughter-islets treated in OCZEM-M as just described are currently continuing to divide and to synthesize and secrete insulin in response to glucose (about 3 mM to about 22 mM range) stimulation for over 17 months in culture. The cells secrete insulin in the amount of about 1 $\mu$IU to 150 $\mu$IU insulin/hour/$10^3$ cells/milliliter of culture medium in a dose related response when challenged with glucose in the range of about 3 mM to about 22 mM. Clonal cultures of human islet cells may be established at any point during the sub-culturing process. Clonal cultures of cells derived from islet cells treated in OCZEM-M as just described are currently continuing to divide and secrete insulin.

Herein, the term "maintenance level of insulin secretion" refers to the amount of insulin secreted into the defined culture medium. In culturing pancreas cells, the preferred medium is OCZEM-M with the medium designated "DMSS" being the next preferred medium. However any of the defined media described herein may be used for pancreas cells.

Preferably, the pancreas cells of the present invention derived from daughter-islets secrete a maintenance level of about 2 $\mu$IU to about 5000 $\mu$IU insulin/hour/$10^5$ cells/milliliter of culture medium. More preferably, the cells secrete a maintenance level of about 10 $\mu$IU to about 2800 $\mu$IU insulin/hour/$10^5$ cells/milliliter of culture medium.

Importantly, the pancreas cells of the present invention, maintained in long-term culture, have the ability to respond to increased glucose and increased amino acid concentrations with increased insulin secretion. The pancreas cells retain these functions for one year and longer in continuous culture. At present there exist continuous insulin secreting cell cultures of this invention that are 4 years old.

In a non-diabetic human, beta-cells within the islets of Langerhans typically are exposed to blood glucose concentrations in the range of about 3 mM to about 8.8 mM. When blood glucose concentration rises above about 5 mM, the normal beta-cells secrete the right amount of insulin to effect the normalization of blood glucose back to 4.4–5.3 mM. Another factor influencing the secretion of insulin in the normal subject is the level of amino acids such as alanine, arginine, and leucine in the blood. Elevated amino acid levels can potentiate the secretion of insulin so that secretion is stimulated at lower glucose levels. Thus, normal beta-cells are exquisitely sensitive to glucose and amino acid levels which rise after a meal, and their secretion of insulin is finely tuned to return those levels to normal.

In contrast, the pancreas cells of human patients who have Type I juvenile onset diabetes are unable to secrete insulin in response to elevated glucose levels. If uncontrolled by exogenous insulin, blood glucose levels in a diabetic may reach 10 mM or greater, at which point glucose is lost through the kidneys leading to dehydration and profound metabolic disturbances. In the clinical management of an adult with Type I diabetes, exogenous insulin is administered at appropriate times and in appropriate amounts to attempt to maintain blood glucose levels between 3.88 mM to 6.66 mM glucose. In a child with Type I diabetes, it is generally considered safer to maintain blood glucose at a higher level, i.e., 6.1 mM to 9.43 mM, because a child may receive too much insulin and be unable to perceive the symptoms associated with dangerously low blood glucose levels. Clearly, exogenous insulin administration is an imperfect substitute for the function of normal pancreatic beta-cells which respond continuously to fluctuating glucose levels with appropriate insulin secretion.

The human pancreas cells of the present invention have the capability to respond in dose-response fashion to increased glucose levels in their culture medium, as depicted in FIG. 11. Moreover, the in vitro response of these cells in long-term culture is comparable to that expected from normal mature human beta-cells in primary culture. The responsiveness of the cells may be tested by several means.

To begin the test, the cells may be placed in fresh defined culture medium of the same type in which they are maintained over the long term. The long-term culture medium preferably contains from about 6.5 mM to about 8.0 mM glucose, most preferably 7.4+/−0.3 mM glucose. Nevertheless, the preferred glucose level in the long-term culture medium is comparable to the high end of the normal range of human blood glucose, so that the cells remain induced for insulin production. The amount of insulin secreted into the defined medium is referred to as the "maintenance level", as described above.

Alternatively, to build up stores of insulin within the cells, and to enhance the cells' responsiveness to glucose, the cells may be "glucose-starved" by incubation in "glucose-poor medium". The term "glucose-poor medium" refers to a culture medium which contains less than the normal physiological concentration of glucose, typically from zero to less than 3 mM glucose preferably about 1 mM to about 2 mM. The cells are incubated for about one to about 16 hours, preferably about 2 hours, in glucose-poor medium prior to the experimental test for response to glucose.

The cells are then placed in a range of glucose concentrations, typically from about 0.5 mM to about 33 mM glucose. As a control, several cultures are not exposed to increased glucose, but rather are placed in fresh "glucose-poor medium" or the regular defined medium containing a high normal physiological concentration of glucose (approximately 7.4 mM–7.7 mM or 7.6±0.2). As defined herein low-glucose or glucose-poor medium is $\leq 2$ mM glucose. Samples of medium are removed at various time points for assay of insulin content. The amount of insulin secreted into the control medium without added glucose, whether glucose-poor or defined medium, is referred to as the "basal level" of insulin secretion for a given test. Basal medium as defined herein is low-glucose or glucose poor medium ($\leq 2$ mM glucose). Maintenance medium is about 7.4 to about 7.6 mM glucose.

Preferably, when exposed to about 6 mM glucose, the cells secrete insulin at about 1.2 to about 2.5 fold the basal level. Also preferably, when exposed to about 6.1 mM to about 17 mM glucose, the cells secrete insulin at about 3 to about 10 fold the basal level. Generally, the pancreatic cells of the present invention respond maximally to 11 mM to 16.5 mM glucose.

This glucose response pattern is comparable to that of freshly resected human insulinomas, enclosed in permselective macrocapsules, perfused in vitro (Altman, J. J. et al. (1984), *Trans. Am. Soc. Art. Organs* 30:382–386). The encapsulated insulinomas were reported to respond maximally to 5.5 mM glucose (220 µIU insulin/ml secreted) and to 16.5 mM glucose (350 µIU insulin/ml secreted).

The pancreatic cells' response to amino acids is tested similarly. The cells are placed in medium containing various concentrations of glucose. Portions of the cultures are exposed to an amino acid such as alanine or arginine, in concentrations ranging from about 0.5 mM to about 40 mm. After an incubation time of about 0.5 to about 24 hours, preferably after 1.5 hours, samples of the medium are assayed for insulin content.

Preferably, when incubated in about 1 mM glucose for 1.5 hours, the pancreatic cells secrete an intermediate level of insulin. When 10 mM alanine is added together with 1 mM glucose, insulin secretion is stimulated approximately 1.13 fold over the intermediate level of secretion. When 20 mM arginine is added together with 1 mM glucose, insulin secretion is stimulated approximately 1.4 fold over the intermediate level of secretion. Preferably, similar effects of amino acids are seen in 2 mM glucose. This amino acid response is comparable to that expected from normal pancreas cells, in which insulin secretion is potentiated by amino acids so that more insulin is secreted at lower levels of glucose.

These tests of human pancreatic cells in long-term culture indicated that the cells of the present invention retain certain characteristics of normal beta-cells, and therefore they may be useful in therapy for diabetes.

Importantly, since the cells respond to physiologically relevant changes in glucose and amino acid concentration, they are good candidates for transplantation into diabetic patients to replace the functions of damaged or destroyed beta-cells.

The cells may be subjected to encapsulation processes, and the resulting capsules may be implanted in the patient. The capsules are porous, to allow glucose from the blood stream to reach the cells, and to allow insulin secreted by the cells to diffuse out of the capsule and into the blood stream. It is expected that the cells will respond to changes in the patient's blood glucose concentration in a similar fashion as they do to glucose concentrations in vitro. Resulting insulin secretion by the cells is expected to normalize the patient's blood glucose level, and the cells will then decrease their insulin secretion accordingly.

It will be apparent to one of skill in the art of cell culture that single-cell sub-clone cultures may be established from the cell cultures of the present invention. There may be advantages to single-cell sub-clone cultures in that the cells of a given culture, being progeny of just one cell, are expected to be homogeneous in their characteristics. Numerous sub-clone cultures may then be screened for various desired characteristics such as rate of proliferation and responsiveness to glucose. An optimal culture may be selected for each projected use, such as implantation within capsules.

It will be apparent to one of skill in the art of the present invention that the herein provided methods may be applied to many additional cell types, such as mammary cells, which have been traditionally difficult to establish and propagate in culture.

The experimental examples set forth below illustrate the practice of this invention.

EXAMPLE 1

This example sets forth a method for establishing human granulosa cells in culture using donor serum in the establishing medium.

Cell source: The cells in this example were obtained from follicular cells which accompanied ova extracted from patients undergoing in vitro fertilization.

Donor serum: Blood was collected from each cell donor 24 hours before ovum retrieval and was allowed to thoroughly clot. The clotted blood was centrifuged at 2700 rpm for 10 min. The clear serum was carefully removed, placed in a sterile Falcon tube and centrifuged again to remove any residual erythrocytes. The serum was used only if there were no signs of hemolysis. The serum was removed, placed in another sterile Falcon tube and heat inactivated at 57° C. for 30 minutes. The heat inactivated serum was filtered with a 0.20 micron Nalgene filter and collected into a sterile Falcon test tube before use in making the BDM and EM.

The formulations for BDM and EM were based on an initial formulation of basal medium designated "IVF Ham's F-10" which was synthesized according to the following protocol:

IVF Ham's F-10: To 1000 ml of Ham's F-10 with L-glutamine (GIBCO, set forth in Formula I below) was added 0.9 grams sodium bicarbonate, 0.075 grams penicillin, 0.075 grams streptomycin, and 0.245 grams calcium lactate. Osmolarity was adjusted to a range between 280 and 285 mOsm with cell culture water (type 1 water, 18 mega-ohm water, GIBCO or M.A. Bio). The medium was filter sterilized with two, 500 ml, 0.20micron Nalgene filter units. The is pH was 7.7.

Formula I

F-10 Nutrient Mixture (Ham)[1]

| Component | mg/L |
|---|---|
| Nonorganic Salts: | |
| CaCl$_2$ (anhyd.) | 33.29 |
| CaCl$_2$.2H$_2$O | — |
| CuSO$_4$.5H$_2$O[a] | 0.0025 |
| FeSO$_4$.7H$_2$O | 0.834 |
| KCl | 285.00 |
| KH$_2$PO$_4$ | 83.00 |
| MGCl$_2$ (anhyd.) | — |
| MgCl$_2$.6H$_2$O | — |
| MgSO$_4$ (anhyd.) | 74.62 |
| MgSO$_4$.7H$_2$O | — |
| NaCl | 7,400.00 |
| NaHCO$_3$ | — |
| Na$_2$HPO$_4$ (anhyd.) | 153.70 |
| Na$_2$HPO$_4$.7H$_2$O | — |
| ZnSO$_4$.7H$_2$O | 0.0288 |
| Other Components: | |
| D-Glucose | 1,100.00 |
| HEPES | — |
| Hypoxanthine | — |
| Hypoxanthine.Na | 4.68 |
| Linoleic acid | — |
| Lipoic acid | 0.20 |
| Phenol red | 1.20 |
| Putrescine.2HCl | — |
| Sodium pyruvate | 110.00 |
| Thymidine | 0.70 |
| Amino Acids: | |
| L-Alanine | 9.00 |
| L-Arginine.HCl | 211.00 |
| L-Asparagine.H$_2$O | 15.01 |
| L-Aspartic acid | 13.00 |
| L-Cysteine | 25.00 |
| L-Cysteine.HCl.H$_2$O | — |
| L-Glutamic acid | 14.70 |
| L-Glutamine | 146.00 |
| Glycine | 7.51 |
| L-Histidine.HCl.H$_2$O[b] | 23.00 |
| L-Isoleucine | 3.60 |
| L-Leucine | 13.00 |
| L-Lysine.HCl | 29.00 |
| L-Methionine | 4.48 |
| L-Phenylalanine | 5.00 |
| L-Proline | 11.50 |
| L-Serine | 10.50 |
| L-Threonine | 3.57 |
| L-Tryptophan | 0.60 |
| L-Tyrosine | — |
| L-Tyrosine.2Na.2H$_2$O | 2.61 |
| L-Valine | 3.50 |
| Vitamins: | |
| Biotin | 0.024 |
| D-Ca pantothenate[c] | 0.715[d] |
| Choline chloride | 0.698 |
| Folic acid | 1.32 |
| i-Inositol | 0.541 |
| Niacinamide | 0.615 |
| Pyridoxine HCl | 0.206 |
| Riboflavin | 0.376 |
| Thiamine HCl | 1.00 |
| Vitamin B$_{12}$ | 1.36 |

[1]Ham R.G. (1963), Exp. Cell Res. 29 515.
[a]Tissue Culture Standards Committee lists this as CuSO$_4$.6H$_2$.
[b]Original formula lists L-Histidine.HCl at 21.0 mg/L.
[c]Values established by the Tissue Culture Committee.
[d]Varies from Tissue Culture Standards Committee value of 0.238 mg/L.

IVF Hams's F-10 was used as the basis for the media described below designated blastocyst development medium (BDM) and establishing medium (EM), and for the media formulations described in Example 2 (DM-1) and in Example 5 (EM-01).

Blastocyst development medium (BDM): 1.5 ml of heat inactivated (37° C., 30 min) donor serum was added to 8.5 ml of IVF Ham's F-10. The pH was 7.35+/−0.6. The medium was filter sterilized with two 0.20 um Nalgene filter units.

Establishing medium (EM): 1.5 ml of donor serum was added to 18.5 ml of IVF Ham's F-10. The pH was 7.2 to 7.45. The medium was filter sterilized with two 0.20 um Nalgene filter units.

Oil plates: Each oil plate was prepared by placing 12 ml of mineral oil equilibrated against IVF Ham's F-10 for about 16 hours in the bottom of a polystyrene resin, "NUNCLON" culture plate ("NUNCLON" tops were not used). Under the oil overlay was carefully placed a bubble of EM or BDM of approximately 0.4 to 0.5 cc which had been equilibrated overnight with 5% $CO_2$/5% $N_2$/90%$O_2$ at 37° C. Each oil plate had 6 bubbles of EM or BDM. The equilibrated oil overlay provided protection against rapid pH changes in the bubbles.

Cell donors: All donors were patients who chose in vitro fertilization and who voluntarily donated follicular cells which were aspirated along with ova and which would otherwise have been discarded after the in vitro fertilization procedure. Prior to ovum retrieval, female patients between the ages of 22 and 43 years were treated with a combined hormonal regimen to stimulate the development of multiple follicles. The treatment typically included leuprolide acetate for midluteal suppression combined with human menopausal hormone (hMG) and follicle stimulating hormone (FSH) for controlled ovarian hyperstimulation. Radioimmune assays (RIA) were used to monitor the serum levels of estradiol and progesterone. Ultrasonic scans were used to assess the number of growing follicles and their size. Thirty-four hours (+/−1 hour) prior to oocyte retrieval, 10,000 IU of human chorionic gonadotropin (hCG) was administered. Follicular contents were aspirated during transvaginal oocyte retrieval, and the follicles were irrigated with 37° C. Dulbecco's solution. The follicles in solution were collected in 15 cc sterile Falcon disposable test tubes and immediately transferred to the embryology lab. It should be noted that no perfumes were permitted in the embryology lab because fumes from certain perfumes were found to affect the viability of cells.

Ovum complexes were identified and transferred to Falcon culture well dishes (#3007) containing 5 cc warm establishing medium (EM). One to 3 ovum complexes were put into each collection dish. An ovum complex includes the ovum, the surrounding zona pellucida, zona radiata, cumulus cells, and attached follicular components. The time limitation for the transfer procedure was 90 seconds in order to minimize pH alterations and temperature fluctuations. The collection dish was immediately placed, with the lid cracked, into a 37° C. incubator containing 5% $CO_2$ (medical grade).

After about 5 to about 30 minutes, the ovum complexes were transferred into EM bubbles on an oil plate. Generally 1 to 3 ovum complexes were placed within a single EM bubble. During this procedure, the EM plate remained outside the incubator no longer than 7 minutes. The oil plate was then placed into a fail-safe container which was gassed with filtered 5% $CO_2$/5% $O_2$/90% $N_2$ medical mixture, sealed and placed into a 5% $CO_2$ incubator at 37° C. for 4.0 to 5.5 hours.

The ovum was then inseminated by the addition of a drop of final sperm suspension to each EM bubble. The amount of sperm added was adjusted to give a final concentration of approximately 50 to 60 million spermatozoa per ml in each EM bubble. The oil plate was incubated overnight as above. The following morning, examination of the EM bubbles showed the presence of two classes of cells: 1) loose cells in the EM, and 2) cells of the zona radiata tightly complexed with the ovum.

At this time point, about 50 to 52 hours after ovum retrieval, non-germ line cells were selected for further culture.

(a) Selection from loose cells after 50 hours in EM: The ovum was aspirated from the EM and incubated according to conventional IVF methods. Non-germ line cells were selected for culture from cells that showed monolayer spreading on the bottom of the plate. Cells with adherent blood clots were avoided. Selected cells were placed in fresh EM bubbles in a freshly equilibrated oil plate. The transfer was done with gentle scraping to loosen the follicular cells from the culture plate. The borosilicate sterile transfer pipette had been precoated with Ham's F-10. "NUNCLON", polystyrene resin culture plates (SECO, Rolling Hills, Pa.), bottoms only, were used for these cultures. Twenty to 50 selected cells were placed in each EM bubble. (i) These cultures were placed into fail-safe containers and flooded with 5% $CO_2$/5% $O_2$/90% $N_2$; then the containers were sealed and placed into a 5% $CO_2$ incubator for 3 days. (ii) The cells were then placed in Falcon #3007 well dishes containing 6 ml of EM and overlain with mineral oil equilibrated with IVF Ham's F-10. Each culture well was originally seeded with 50 to 100 cells and maintained under the above conditions for 30 days. During the 30 day establishment period, the cultures were fed every 5 to 6 days with 1 ml of fresh EM (i.e., in a well containing 6 ml, 1 ml was removed and replaced). After 15 days, in certain cultures it was apparent that cells had proliferated to the point that sub-culture was necessary (i.e., the number of cells had increased 3 to 4 fold). The cells were gently scraped from the bottom of the dish and small groups of cells were transferred to new culture dishes containing EM as above.

(b) Selection from cells adhering to ovum after 50 to 52 hours in EM: The ovum plus the complexed zona radiata cells were carefully transferred to blastocyst development medium (BDM) bubbles in a BDM oil plate. Subsequently, the adherent zona radiata cells were manually peeled from the ovum by gently drawing the ovum plus adherent cells into the orifice of a 27½ gauge hypodermic needle and gently expelling the egg.

This stripped the adherent zona radiata cells from the smoother membrane, zona pellucida, surrounding the ovum. (The peeled ovum was incubated and prepared for implantation or cryopreservation according to conventional in vitro fertilization methods.) From the stripped zona radiata cells in BDM, cells were selected according to the above criteria and established in culture as described in 1 (a) (i, ii) above.

After a total of 30 days in EM culture, cells were subcultured as follows in Example 2.

EXAMPLE 2

This example sets forth a method for maintaining and propagating hormone-secreting cells in long-term culture.

Upon completion of the initial 30 days of establishing culture (Example 1), the sub-culture selection process was begun. Initial sub-cultures (SC-1) of small groups of cells were manually selected. Cell selection was performed under phase optics according to selection criteria illustrated in FIGS. 2, 3, and 4. The circled clumps of cells are representative of the type of cell clumps that were chosen as most likely to have hormone-secreting potential. Small clumps of 2 to 12 cells were chosen, most often clumps of 4 to 5 cells. Typically, the cells in the selected clumps were arranged in a semi-linear fashion, i.e., touching each other in a "string-of-pearls" type arrangement. The selected cells were approximately spheroid or ovoid in shape, and were of approximately homogeneous size and shape. The selected cells typically had a smooth appearing membrane, and a smooth-appearing rather than a granular cytoplasm.

When it was desired to assay for hormone content within a short time period, the selected clumps were grouped into cultures of 50 to 150 cells each, designated SC-1, in a medium composed of 40 cc IVF Ham's F-10+0.25 gm BSA in Falcon #3037 tissue culture wells with no oil overlay.

Each culture was placed in an individual well containing 5 ml of medium, the cultures were flooded with medical blood gas mixture (supra), and placed in a sealed container within a 37° C. incubator. The cultures were maintained in this medium for 3 days, after which hormone content of the medium was assayed.

Alternatively, selected clumps were grouped into smaller starting sub-cultures of 10–15 cells, also designated SC-1. These groups were placed in defined medium (DM-1) formulated as follows.

Defined medium-1 (DM-1) : 100 ml of IVF Ham's F-10 (see example 1 above) was mixed with 100 ml nutrient Ham's F-12, HEPES and sodium bicarbonate buffered and glutamine supplemented (7.35 mM glutamine), Sigma, as set forth in Formula II below. To this was added 30 ml tissue culture water (Sigma), 7.2 grams cell culture tested BSA (Fraction V, Sigma), 1500 IU penicillin-G, and 1.5 mg streptomycin. The medium was equilibrated overnight at 37° C. in a 5% $CO_2$ atmosphere before use. The final osmolarity was 272+/−1 mOsm. The pH was adjusted to 7.65. The medium was filter sterilized with one 0.45 um and one 0.20 um Nalgene filter unit.

Formula II

| Component | (F-12 with sodium bicarbonate and 25 mM HEPES w/o L-glutamine) g/L |
|---|---|
| Inorganic Salts: | |
| Calcium Chloride.$2H_2O$ | 0.0441 |
| Cupric Sulfate.$5H_2O$ | 0.0000025 |
| Ferrous Sulfate.$7H_2O$ | 0.000834 |
| Magnesium Chloride.$6H_2O$ | 0.123 |
| Magnesium Sulfate (anhydrous) | — |
| Potassium Chloride | 0.224 |
| Potassium Phosphate Monobasic (anhyd.) | — |
| Sodium Bicarbonate | 1.176 |
| Sodium Chloride | 7.1 |
| Sodium Phosphate Dibasic (anhyd.) | 0.14204 |
| Zinc Sulfate.$7H_2O$ | 0.000863 |
| Amino Acids: | |
| L-Alanine | 0.009 |
| L-Arginine.HCl | 0.211 |
| L-Asparagine $H_2O$ | 0.01501 |
| L-Aspartic acid | 0.0133 |
| L-Cysteine.HCl.$H_2O$ | 0.035 |
| L-Glutamic acid | 0.0147 |
| Glycine | 0.00751 |
| L-Histidine.HCl.$H_2O$ | 0.02096 |
| L-Isoleucine | 0.00394 |
| L-Leucine | 0.0131 |
| L-Lysine.HCl | 0.0365 |
| L-Methionine | 0.00448 |
| L-Phenylalanine | 0.00496 |
| L-Proline | 0.0345 |
| L-Serine | 0.0105 |
| L-Threonine | 0.0119 |
| L-Tryptophan | 0.00204 |
| L-Tryosine 2Na.$2H_2O$ | 0.00778 |
| L-Valine | 0.0117 |
| Vitamins: | |
| D-Biotin | 0.0000073 |
| Choline chloride | 0.01396 |
| Folic acid | 0.00132 |
| myo-Inositol | 0.018 |
| Niacinamide | 0.000037 |

-continued

| Component | (F-12 with sodium bicarbonate and 25 mM HEPES w/o L-glutamine) g/L |
|---|---|
| D-Pantothenic Acid (hemicalcium) | 0.00048 |
| Pyridoxine.HCl | 0.000062 |
| Riboflavin | 0.000038 |
| Thiamine HCl | 0.00034 |
| Vitamin $B_{12}$ | 0.00136 |
| Other: | |
| D-Glucose | 1.802 |
| HEPES | 5.958 |
| Hypoxanthine | 0.00408 |
| Linoleic Acid | 0.000084 |
| Phenol Red (sodium) | 0.0013 |
| Putrescine.HCl | 0.000161 |
| Pyruvic Acid (sodium) | 0.11 |
| Thioctic Acid | 0.00021 |
| Thymidine | 0.60073 |
| Add: | |
| L-Glutamine | 0.146 |
| Specifications: | |
| pH at 25° C. (with sodium bicarbonate) | 7.3 ± 0.3 |
| Osmolality - mOsm/Kg $H_2O$ (with sodium bicarbonate) | 300 ± 5% |

These sub-cultures were grown for 14 to 15 days in DM-1; medium was refreshed every 5 to 6 days. During this time, the cell number typically increased about ten to thirty fold. It was found that the SC-1 cultures which had been established from only 10–15 starting cells also secreted hormones which were detectable by radio-immune assay within only a few days.

After about 15 days, each SC-1 culture was divided into about 4 to 6 second sub-cultures (SC-2).

Cells in SC-2 were propagated and sub-cultured as above more than 20 times. Medium was collected from each sub-culture at regular intervals and assayed for the presence of secreted estradiol ($E_2$), progesterone, luteinizing hormone (LH), follicle stimulating hormone (FSH), thyroid stimulating hormone (TSH), prolactin, testosterone and the β-chain of human chorionic gonadotrophin (B-hCG). Quantitative radioimmune assays (RIA) were employed as described in *Radioassay Systems in Clinical Endocrinology,* 1981, Ed. G. E. Abraham, {Basel: Marcel Dekker}, pp. 475–529. Progesterone, testosterone, estradiol, prolactin, thyroid stimulating hormone and luteinizing hormone were assayed by the Coat-a-Count procedure (Diagnostic Products Corp., Los Angeles). Follicle-stimulating hormone and B-hCG were assayed by the SERONO MATAclone procedure (Serono, Italy).

Results from assays of secretion from various cultures after more than 4 months in continuous serial sub-culture are shown in Table 1.

TABLE 1

| Sub-cultures (after 4+ months) Granulosa Cell Cultures | No. of Cells | Synthesis Days | RIA Analyses | | | | |
|---|---|---|---|---|---|---|---|
| | | | $E_2$ pg/ml | Progesterone ng/ml | β-hCG mIU/ml | LH mIU/ml | FSH mIU/ml |
| 100B-4 | $10^6$ | 5 | 2576 | 453.8 | 0 | 0 | 0 |
| 100B-5-04-03 | $10^3$ | 9 | <20 | 14.1 | 0 | <1.8 | 1.71 |
| 100B-5-04-05 | $10^3$ | 9 | 21 | 51.2 | 0 | 0 | 2.59 |
| 100C-2-02-B1 | $10^3$ | 9 | <5 | 0.3 | 0 | 0 | 3.11 |
| 100B-5-OR-04 | $10^6$ | 10 | 233 | 425.8 | 0 | <1.8 | 3.92 |
| 100B-5-OR-01-D | $10^3$ | 3 | 34 | 59.5 | 0 | 0 | 0 |
| 100B-5-OR-01-C | $10^3$ | 3 | 35 | 48.9 | 0 | 0 | 0 |
| 100B-5-OR-02-A | $10^6$ | 3 | 41 | 65.8 | 0 | 0 | 3.74 |
| 100B-5-OR-02 | $10^6$ | 6 | 402 | 202.5 | 0 | 0 | 0 |

Conclusions: Using this method, human follicular cells were propagated in culture and transferred to serial subcultures which continued to proliferate and to secrete hormones. Typically, after greater than 4 months in continuous sub-culture, several of the cell cultures secreted moderate to high levels of estrogen, progesterone, and FSH. When 100 mg/ml testosterone (sigma T-5641) was added to provide a required substrate for steroid production, these subcultures were found to continue to secrete hormones for as long as 16 months after the cells were first placed in culture.

EXAMPLE 3

This example demonstrates the level of cell propagation achieved in cultures of hormone-secreting cells.

Cell counting methods: For seeding original primary cultures, as in Example 1, and first sub-cultures, as in Example 2, cell number was established by direct counting through an inverted phase microscope as the cells were being selected. At various time points after seeding, cell number was established by counting and averaging numbers of cells contained in multiple drops on a Makler counting chamber (Sefi Medical Instruments, Haifa, Israel). The Makler counting chamber has a grid 0.01 mm$^2$×0.01 mm depth.

Representative samples of cell concentrations were obtained either directly from suspension cultures or from cell populations that had been detached from substrate.

Results: During the first six days in the first sub-culture, SC-1, cell number typically increased about 3 fold. Typical SC-1 results are shown below in Table 2.

TABLE 2

| Starting cell number | Cell number after 6 days |
|---|---|
| SC-1a | 100 | 350 |
| SC-1b | 50 | 156 |
| SC-1c | 100 | 294 |
| SC-1d | 100 | 271 |

During the later part of SC-1, and during subsequent sub-cultures, cell proliferation rate typically increased to a doubling time of approximately three days.

As shown in Table 1, Example 2, cells also produced hormones during the days they proliferated.

EXAMPLE 4

This example describes the establishment of follicular cells in culture using non-homologous human serum.

Follicular cells from three individual cell donors were established in culture as described in Example 1, with the exception that the cells were placed directly into DM instead of EM, and maintained in DM for 7 days. Subsequently, the cells were transferred into a second medium which was either DM or EM containing, in place of cell donor serum, serum from a different individual. The serum donors were women participating in the IVF program who were being pre-treated with the hormonal regimen as described. The hormonal profile for donor serum "A" was within the normal range for women undergoing this hormonal pre-treatment; the hormonal profile for donor serum "B" was within the "hyperstimulated" range. Hyperstimulation, which occurs for unknown reasons in certain patients undergoing regular IVF hormonal pretreatment, is marked by high levels of estrogen and an increase in progesterone to about 1.0 ng/ml in the serum. The cells were maintained in either DM or in EM (non-homologous serum) for 2 to 3 weeks, after which they were subcultured as described in Example 2.

Results: Follicular cells were successfully established in culture and secreted hormones as shown in Table 3.

TABLE 3

| Culture # | Second medium | Prog (ng/ml) | $E_2$ (pg/ml) |
|---|---|---|---|
| 1 | DM | 59.5 | 34 |
| 1 | EM (serum A) | 48.9 | 35 |
| 2 | DM | 86.4 | 240 |
| 2 | EM (serum B) | 83 | 585 |
| 2 | EM (serum A) | 82.7 | 267 |

Conclusions: Cells can be established in EM containing non-homologous serum, however the level of hormone secretion is influenced by the level of estrogen and may also be influenced by the progesterone level in the serum employed.

EXAMPLE 5

This example describes a method for establishing, maintaining, and propagating hormone-secreting cells in a culture medium not containing serum.

Follicular cells were obtained from a donor as described in Example 1. The serum of this patient contained a significant amount of anti-sperm antibody (greater than 20% of the total IgG was anti-sperm). Therefore, in order to optimize the insemination of the ova from this patient, donor serum was not included in any of the media used during the IVF procedure.

Follicular cells were obtained, selected, and established in culture as described in Example 1 with the exception that BSA supplemented medium (EM-1) was used in place of donor-serum containing medium (GM and EM). EM-1 consisted of IVF Ham's F-10 (see Example 1) plus BSA (fraction V, Sigma) added to a final concentration of 0.5% to 1.0%. The osmolarity of EM-1 was 273 mOsm; the pH was 7.41.

Established follicular cells were maintained, sub-cultured, and propagated in culture as described in Example 2.

Results: Under these conditions, cells proliferated and secreted hormones successfully, as shown in Table 4. Results in Table 4 were obtained during seventh or eighth sub-cultures (SC-7 and SC-8). Control culture 100B-5-OR-04 was established in medium with donor serum (EM); cultures 100B-5-OR-01 and 100B-5-OR-02 were established in medium without serum (DM).

TABLE 4

| Culture | $E_2$ (pg/ml) $10^6$ cells | Prog (ng/ml) $10^6$ cells | Cell Number Determination SC start | Cell Number Determination 3 days\SC |
|---|---|---|---|---|
| 100B-5-OR-04 | 233 | 425.8 | 100 | 189 |
| 100B-5-OR-01 | 34 | 59.5 | 100 | 171 |
| 100B-5-OR-02 | 41 | 65.9 | 100 | 163 |

None of the cultures secreted a detectable amount of the gonadotrophins FSH, LH or β-hCG.

Conclusions: Cells which are initially established in DM exhibit a rate of proliferation which is comparable to that of cells which are initially established in EM. Cells established in DM, however, exhibit reduced basal steroid hormone production even after 7 or 8 rounds of serial sub-culture. Therefore, cells established in DM are advantageous for use in assays such as gonadotrophin bioassays, which are favored by low basal steroid secretion.

EXAMPLE 6

This example describes the maintenance and propagation of cells in defined medium containing a serum substitute (DMSS).

Follicular cells were established in culture as described in Example 1. The cells were then subcultured as described in Example 2 with the exception that the amount of BSA was reduced as compared to the defined culture medium (DM-1) and a serum-substitute was added ["SERU-MAX", Lot No: 107-F-4607, Sigma]. "SERU-MAX" contains, among other components, growth factors such as bovine fibroblast growth factor, murine epidermal growth factor, and bovine insulin, as well as ethanolamine, selenium, transferrin, and hydrocortisone. The "SERU-MAX" composition is set forth in Formula III. This medium formulation, DMSS, represents a more defined medium than DM because a portion of the BSA is replaced by a more defined supplement ("SERU-MAX"). The formulation of DMSS is described below:

Defined medium, serum substitute (DMSS): To 100 ml Ham's nutrient F-12, HEPES and sodium bicarbonate buffered, was added 5 ml L-glutamine supplement to bring the glutamine level to 7.35 mM total (Sigma), 17 ml cell culture tested distilled water (Sigma), plus 0.25 grams cell culture tested BSA (fraction V, Sigma), 2.5 mM Na pyruvate, 1500 IU penicillin-G, 1.5 mg streptomycin, and 10% "SERU-MAX" (Sigma). "SERU-MAX" lot number analysis 107F-4607 is available from Sigma Chemical Co, St. Louis, Mo. The final osmolarity was 272±1 mOsm. The pH was adjusted to 7.65. Final volume, 136 ml, was filter sterilized with two 0.20 um Nalgene filter units.

Formula III

"SERU-MAX" is fetal bovine serum supplemented with: bovine extract, bovine fibroblast growth factor, murine epidermal growth factor, bovine insulin, bovine serum albumin-fraction V, ethanolamine, sodium selenite, human transferrin and hydrocortisone. The product profile formula, obtained from Sigma, is set forth below.

| Parameter/ [Method] | Specification | Observed Results |
|---|---|---|
| Sterility [U.S. Pharmacopeia Vol. XXI] | Sterile | Sterile |
| Mycoplasma [Screened] | Negative | Negative |
| Bacteriophage [Screened] | Negative | Negative |
| Adventitious Viral Agents [AVA] [9 CFR[A]-113.53] | | |
| BVD[B] | Negative | Negative |
| IBR[C] | Negative | Negative |
| PI3[D] | Negative | Negative |
| Endotoxin [Limulus Amebocyte Lysate, Sigma No. 210, E-Toxate] | | 0.375 ng/ml |
| Hemoglobin [Colorimetric-Peroxidase Procedure] | ≦20.0 mg % | 18.2 mg % |
| Electrophoretic Identity [Cellulose Acetate; Barbital Buffer pH 8.6] | Characteristic | Characteristic |
| Osmolality [Vapor Pressure Analysis] | 240–300 mOsm/Kg $H_2O$ | 299 mOsm/Kg $H_2O$ |
| pH at 25° C. | 7.0–8.0 | 7.42 |

[A]U.S. Code of Federal Regulations
[B]Bovine Viral Diarrhea
[C]Infectious Bovine Rhinotrecheitis
[D]Parainfluenza Type 3

The following chemical data were determined by SMA-24 analysis:

| Parameter | Observed Results |
|---|---|
| Glucose | 100 mg % |
| Radium | 138 mEq/L |
| Potassium | 12.3 mEq/L |
| Chloride | 103 mEq/L |
| $CO_2$ | 13 mEq/L |
| Blood Urea Nitrogen [BUN] | 17 mg % |
| Creatinine | 3.3 mg % |
| Uric Acid | 2.5 mg % |
| Calcium | 14.5 mg % |
| Phosphorus | 10.5 mg % |
| Total Protein | 3.7 g % |
| Albumin | 2.7 g % |
| Alkaline Phosphatase | 318 mU/mL |
| Total Bilirubin | 0.2 mg % |
| SGOT | 45 mU/mL |
| Gamma GT | 3 mU/mL |
| Lactate Dehydrogenase [LDH] | 539 mU/mL |
| Cholesterol | 35 mg % |

-continued

| Parameter | Observed Results |
| --- | --- |
| Triglycerides | 2 mg % |
| Total Iron | 206 μg % |
| Ionized Calcium | 8.8 g % |
| Protein Electrophoresis | |
| Serum Total Protein | 3.7 g % |
| Serum Albumin | 2.5 g % |
| Globulins | |
| Alpha 1 | 0.0 g % |
| Alpha 2 | 0.8 g % |
| Beta | 0.4 g % |
| Gamma | 0.0 g % |

AMINO ACID ANALYSIS

| Free Amino Acid | Assayed Value μmoles/mL | Free Amino Acid | Assayed Value μmoles/mL |
| --- | --- | --- | --- |
| Alanine | 0.95 | Leucine | 0.24 |
| Arginine | <0.1 | Lysine | 0.18 |
| Asparagine | * | Methionine | <0.1 |
| Aspartic Acid | — | Phenyl-alanine | 0.11 |
| Cystine | 0.07 | Proline | * |
| Glutamine | * | Serine | * |
| Glutamic Acid | * | Threonine | * |
| | | Tryptophan | — |
| Glycine | 0.56 | Tyrosine | 0.11 |
| Histidine | 0.12 | Valine | 0.33 |
| Isoleucine | 0.15 | | |

*Formed inseparable peaks

Cell Culture Testing

The normal growth promoting capabilities of this serum have been assessed using the following cell lines:
1. LLC MK,
2. Vero
3. 1929

Results: Cell proliferation in DMSS proceeded comparably to that of control cell cultures grown in DM-1. Prolactin synthesis increased slightly but not significantly (0.4% in response to the Seru-Max). Progesterone and estradiol synthesis levels were not altered in DMSS as compared to DM-1 controls. In contrast, when 10% or 15% fetal calf serum (FCS) was used in place of Seru-Max, hormone content of the cultures was near zero and cell proliferation was significantly slower (data not shown).

Conclusions: The use of defined medium with serum supplement is advantageous over the use of FCS supplemented serum for human hormone-secreting cell propagation and maintained hormone secretion potential.

EXAMPLE 7

This example describes the establishment, maintenance, and propagation in culture of follicular cells which were not exposed to sperm.

Follicular cells were obtained as described in Example 1 from patients who prior to ovum extraction had elected to have only a specific number of retrieved ova fertilized. This situation allowed for the selection of follicular cells which were treated as described in Example 1 with the exception that they had not been exposed to sperm.

Cells were selected as in Example 1(a) from loose cells in EM bubbles. (It was impractical to retrieve cells surrounding the ovum as in Example 1(b), possibly because exposure to sperm is required to loosen the cells of the zona radiata.) Fewer cells were obtained by this method as compared to Example 1, however the cultures were successful. Initial cell counts showed a recovery of only 12 to 27 cells per EM bubble with 3 complexes per bubble. This contrasted to the complexes that had a sperm suspension added (same cell donor) in which the initial cell recovery from each EM bubble for primary culture was 131 to 198 cells. The non-sperm exposed cultures did eventually become established, however an additional 1.5 to 2 weeks were required for satisfactory cell culture establishment. The non-sperm exposed cultures were maintained for approximately 5 weeks, during which time their hormone-secretion profile was comparable to that shown in Table 1 for sperm-exposed cultures.

EXAMPLE 8

This example describes cells maintained in culture which respond to stimulation by gonadotrophin and by cAMP with increased hormone secretion.

Ovarian follicular cells, lines 100B-OR-5A, 100B5-OR-B, and 100B5-OR-D, were established in culture as described in Example 1 and maintained and sub-cultured as described in Example 2. From these lines were created sub-cultures designated 1, 2, and 3 respectively, which were employed in the stimulation protocol described below.

(a) Gonadotrophin stimulation: Human chorionic gonadotrophin (hCG; Sigma) was added to the culture medium (DM-1) in the amount of 750 ng/ml. After 70 to 76 hours, progesterone content of the medium was increased approximately two-fold over control. Estradiol synthesis was also stimulated by hCG, leading to an increased estradiol content of 0.4 to 0.5 fold over control within 30 hours. Results are shown in Table 5 below:

TABLE 5

| | Prog (ng/ml) | | $E_2$ (pg/ml) | |
| --- | --- | --- | --- | --- |
| Culture | No hCG | + hCG | No hCG | + hCG |
| 1 | 5.8 | 12.1 | 26 | 43 |
| 2 | 9.0 | 19.8 | 59 | 76 |

(b) cAMP stimulation: Cultures were exposed to 1 mM 8-Br-cAMP (Sigma) or to FSH (1IU/ml; Metrodin [urofollitropin], Lot No. 07321070, Serono, Italy). As shown in Table 6 below, progesterone content in the cultures was increased 5 to 11 fold in response to 24 hours of cAMP stimulation. FSH stimulation for 48 hours led to an increase in progesterone content of 6.5 to 7.7 fold.

TABLE 6

| | Prog (ng/$10^6$ cells) | | |
| --- | --- | --- | --- |
| Culture | Nothing added | 8-Br-cAMP | FSH |
| 1 | 3.0 | 24.5 | 17.2 |
| 2 | 1.4 | 12.9 | 10.8 |
| 3 | 2.9 | 20.8 | 18.9 |

Conclusions: Follicular cells in culture responded to stimulation by gonadotrophin in a manner comparable to their counterparts in vivo, i.e., granulosa cells. This indicates that follicular cells propagated in vitro according to this invention express a differentiated characteristic of granulosa cells, and are thus potentially useful in bioassays for gonadotrophin potency as well as for chemical toxicity.

EXAMPLE 9

This example sets forth a method to assay the potency of a preparation of gonadotrophin.

Follicular cells were obtained from a donor who had been pre-treated with an ovary-stimulating hormonal regimen that did not include hCG. The follicular cells had therefore not been exposed to high levels of gonadotrophin prior to selection for culture, and did not secrete high basal levels of progesterone.

The cells were established in culture as in Example 1 and propagated in culture as in Example 2 and Example 6. The amount of progesterone secreted by these cells into a culture medium not containing gonadotrophin was typically undetectable, but a significant amount of estradiol was synthesized.

The gonadotrophin to be bio-assayed (e.g., commercially available FSH preparations) is added to the cell culture; after exposure periods of approximately 24, 48 and 72 hours hormonal content in the culture medium is measured and compared to control. The potency of the gonadotrophin in this in vitro bio-assay is initially related to the FSH values obtained by high-performance liquid chromatography (HPLC; Stone, B. A., et al., 1990, supra). In subsequently employing this bio-assay, the relative potency of a gonadotrophin preparation is obtained by fitting the bio-assay numerical values to standard curves prepared by comparison of bio-assay values and HPLC values.

EXAMPLE 10

This example describes an in vitro bioassay for the potential toxicity of drugs and other chemical compounds.

Ovarian follicular cells were established in culture as described in Example 1 and maintained and sub-cultured as described in Example 2. Sub-cultures secreted progesterone and estrogen at levels comparable to those shown in Table 1.

In order to assess the potential toxicity of a drug, the cells are contacted with the drug to be tested and with a control compound known to be non-toxic. The cells contacted with a non-toxic compound continue to secrete steroid hormones at basal levels. When the experimental drug is toxic, the level of hormone secretion is reduced as compared with control.

EXAMPLE 11

This example sets forth a method to establish and propagate in culture cells from primary follicles.

Primary ovarian follicles were obtained from two donors who were undergoing ovariectomy and who had not been pre-treated with an ovary-stimulating hormonal regimen.

Primary follicles were manually isolated from small pieces of ovarian tissue. The primary follicle complex was placed into culture and maintained in culture for 6 weeks in the medium designated DMSS (see Example 6). After 5 weeks in culture, the cells were found to secrete estradiol plus a detectable amount of progesterone.

TABLE 7

| Sub-cultures (after 4+ months) Primary Follicles (Primary culture — after 9 days of culture) | No. of Cells | Synthesis Days | Primary Follicle | | | | |
|---|---|---|---|---|---|---|---|
| | | | $E_2$ pg/ml | Progesterone ng/ml | β-hCG mIU/ml | LH mIU/ml | FSH mIU/ml |
| | 6 follicles total | 3 | 134 | 3.2 | 0 | 0 | 0 |
| | 4 follicles total | 3 | 77 | 2.3 | 0 | 0 | 0 |

EXAMPLE 12

This example sets forth a method to establish and propagate in culture hormone-secreting cells of trophoblastic origin.

Trophoblastic cells were obtained from a cell donor undergoing surgery for an ectopic pregnancy. A number of the trophoblastic cells were placed directly into EM as described in Example 1 and further cultured in DM as in Example 2. A second group of trophoblastic cells were placed directly into an alternative type of defined medium containing serum substitute (DMSS, formula given in Example 6, supra) and further cultured as in Example 2, with the exception that the growth medium was DMSS.

Results: The trophoblast cells typically proliferated successfully in culture under both the above described conditions. After 6 days in SC-3 subcultures the medium was assayed for the hormones listed in Table 8 below.

TABLE 8

| 6 weeks synthesis after 5 weeks of culture | FSH mIU/ml | $E_2$ pg/ml | β-hCG mIU/ml | Progesterone ng/ml | Testosterone ng/ml | TSH mIU/ml |
|---|---|---|---|---|---|---|
| SREP-1-0 | .14 | 2.83 | 43.9 | 7.5 | 0.1 | 0.27 |
| SPEP-2-02 | 0.17 | 2.63 | 37.6 | 5.8 | 0.13 | 0.58 |

After 5 weeks in culture, the trophoblast cells maintained the secretion of significant levels of β-hCG, (i.e., 43.9 mIU/10⁶ cells/10 ml/6 days).

EXAMPLE 13

This example sets forth a method for establishing, maintaining, and propagating gonadotrophin secreting pituitary cells in culture.

Segments of pituitary macroadenoma were obtained from a male donor undergoing trans-sphenoidal pituitary surgery. Small clumps of cells were teased from the surrounding tissue and manually isolated via dissection using sterile fine glass needles. These small segments (about 0.5 to 1.0 mm diameter) were placed into individual wells containing DMSS (see Example 6). Several individual cultures representing cells selected from disparate tumor regions were thus formed. After 6 hours in primary culture, the medium was changed, and after a further 42 hours, medium samples were taken (48 hours total time in primary culture; 42 hours synthesis time). As shown in Table 9, all the initial cultures secreted high levels of luteinizing hormone and detectable levels of FSH and progesterone. Three of the cultures also secreted detectable levels of β-hCG. Notably, there was no detectable amount of prolactin secretion, indicating the cells had no lactotroph component, and suggesting that they were of pure gonadotroph lineage.

A cell line is established which secretes a therapeutically useful form of human gonadotrophin. The gonadotrophin is isolated from the medium surrounding the cell cultures and used in the preparation of a medical composition for the pretreatment of women for the in vitro fertilization procedure.

EXAMPLE 14

This example describes a method to establish, maintain and propagate human endometrial cells in vitro.

Endometrial cells were obtained from a woman donor undergoing endometrial biopsy.

Cells were manually isolated. Groups of cells were placed into individual wells and subsequently selected for further culture on the basis of their hormone secretory activity, as determined by RIA of the media. Selected cell groups were established in culture as described in Example 1 and propagated in culture as described in Example 2. As shown in Table 10, after greater than 4 months in culture, two of the cell lines continued to secrete very significant amounts of estrogen and progesterone. Thus, these cell lines are useful for the production of human sex steroid hormone for therapeutic use.

TABLE 9

| 42 hrs. synthesis | $E_2$ pg/ml | LH mIU/ml | Testosterone ng/ml | FSH mIU/ml | Progesterone ng/ml | β-hCG mIU/ml | Prolactin ng/ml |
|---|---|---|---|---|---|---|---|
| D/A Macro -01 | 0 | 123.2 | 0 | 4.09 | 0.2 | 2.6 | 0 |
| D/A Macro -02 | 0 | 42.5 | 0 | 4.19 | 0.11 | 2.7 | 0 |
| D/A Macro -03 | 1 | 71.8 | 0 | 5.23 | 0.1 | 3.1 | 0 |
| D/A Macro -04 | 0 | 40.6 | 0 | 5.16 | 0.3 | 0 | 0 |
| D/A Macro -05 | 2 | 71.8 | 0 | 5.48 | 0.1 | 0 | 0 |
| D/A Macro -06 | 0 | 53.2 | 0 | 3.76 | 0.1 | 0 | 0 |

After 15 days in culture (10 days synthesis time), the cells continued to secrete hormones. The values for D/A Macro-05, for example, were: LH, 11.3; FSH, 4.04; B-hCG, 5.9 (mIU/ml). After 28 days in culture (8 days synthesis time) the -05 culture contained 3.0 mIU/ml of LH, but the other hormones 15 were undetectable. In contrast, "blastema-like" cell clusters, as illustrated in FIGS. 9 and 10, were transferred to separate cultures at culture day 20, and were found to secrete relatively large amounts of hormone. For instance, two such "blastema" groups combined in one culture dish secreted 3.0 mIU/ml of LH over a period of 8 days. Given the relatively small number of cells in the culture, this represents a large amount of hormone secretion, and suggests that the "blastema" cells represented the most productive members of the primary cultures.

TABLE 10

| Sub-cultures (after 4+ months) | | | Endometrium | | | | |
|---|---|---|---|---|---|---|---|
| Endometrium (2nd subculture) | No. of Cells | Synthesis Days | $E_2$ pg/ml | Progesterone ng/ml | β-hCG mIU/ml | LH mIU/ml | FSH mIU/ml |
| PRUE-02-1 | 10⁶ | 3 | 1415 | 150.8 | 0 | <1.8 | 2.91 |
| POIE-A | 10³ | 3 | 20 | 0.3 | 0 | 0 | 0 |
| POIE-OR | 10¹² | 6 | 9039 | 1173.4 | 0 | <1.8 | 2.46 |

EXAMPLE 15

This example describes methods for the cryopreservation of hormone-secreting cells.

Follicular cells were placed in 3 alternative cryopreservative media:
A) 80% DMSS, 10% dimethylsulfoxide (DMSO; cell culture tested, Sigma)), 10% glycerol (Sigma Grade, Sigma)
B) Test-yolk Buffer (Irvine Scientific, CA) plus 15% glycerol C) 87.5% DMSS (containing 2% BSA and 3.4% sucrose), plus 12.4% 1,2-propanediol.

All solutions were slowly filtered with a sterile 0.20 um Nalgene filter and equilibrated with 5% $CO_2$/5% $O_2$/90% $N_2$ (medical gas mixture) for 16 to 24 hours. The cells in cryopreservatives A or B were frozen at a rate of approximately $-1°$ C. per minute to a temperature of $-34°$ C. and stored under liquid nitrogen.

For cryopreservative C, the cells were processed according to the following protocol:

1. 10 ml DMSS+2% BSA, Fraction V (Cell Culture tested, Sigma); 12 minute incubation of $3 \times 10^6$ cells. 37° C. (36 to 37° C.) range.
2. 10 ml [8.75 ml DMSS+2% BSA+1.24 ml 1,2-propanediol (sigma)] 12 min incubation, gentle 1 minute swirling; $3 \times 10^6$ cells; room temp (=35° C.+/−1°)
3. 10 ml [sol.B above+0.34 grams sucrose (cell culture tested, Sigma) ], 12 min incubation, gentle swirling for 1 min; $3 \times 10^6$ cells; room temp (=35°+/−1° C.).
4. Load into 3 cryovials at approximately $10^6$ cells per 1.5 ml of solution C.
5. Cool at 4° C. for 10 min.

Freezing program for Planer Cell Freezer R204; Liquid/Vapor Phase Nitrogen (PLANER Products Ltd.)

Ramp 1: −2° C./min down to −7° C.+/−0.5° C.

Ramp 2: Hold −7° C., 15 min, $N_2$ vapor.

Seed (begin crystallization) at the top of meniscus in the freezing vial at the beginning of Ramp 2 by touching the top of the meniscus with forceps that have been pre-chilled in liquid $N_2$ vapor.

Ramp 3: −0.3° C./min down to −34° C.

Ramp 4: Hold at −34° C. for 30 minutes, then quickly transfer the cryovials to the $N_2$ vapor storage cryotank.

Thawing for freezing method using cryopreservative C:
Thawing solutions:

Solution a: DMSS+2% BSA

Solution b: 1.0 ml of solution A+0.68 grams sucrose

Solution c: 8.8 ml of Solution B+1.2 ml 1,2-propanediol.

All solutions were sterile filtered with a 0.20 um Nalgene filter. The following thawing solutions were prepared in 15 ml Falcon test tubes .

|  |  | Solution b |  | Solution c |
|---|---|---|---|---|
| Solution | T1 | 0 ml | + | 6 ml |
|  | T2 | 2 ml | + | 4 ml |
|  | T3 | 3 ml | + | 3 ml |
|  | T4 | 4 ml | + | 2 ml |
|  | T5 | 5 ml | + | 1 ml |
|  | T6 | 6 ml | + | 0 ml |

The thawing solutions were equilibrated in loose/open-top test tubes with medical gas mixture. The frozen cyrovial was quickly thawed in a 30° C. water bath. The vial was opened and the cells immediately transferred to 6 ml medium "T1" in a Nunculon petri dish and placed in a gassed (medical gas mixture) sealed glass container for 8 minutes at room temperature.

The cells were transferred to a second Nunculon (bottom) culture dish with 6 ml of T1 solution, regassed, and incubated for another 8 minutes. This step was repeated for each of the thawing solutions (T2–T6). The thawed, rehydrated cells were transferred to 25 $cm^2$ Falcon tissue culture flasks containing 10 to 15 ml of DMSS plus 10% Hybridoma Enhancing Supplement (H6020 or H8142, Sigma).

Cells preserved in cryopreservatives A or B were thawed after one month by placing the frozen cryovial in a 36° C. water bath.

The thawed cells were immediately transferred to 25 $cm^2$ Falcon tissue culture flasks containing 15 ml DMSS.

Eighty percent of the thawed cells were found to be viable via the trypan blue dye exclusion test. After one week in culture, the thawed cells typically proliferated at a rate comparable to the cultures from which they originated, and retained the hormone-secretion profiles of their respective parent cultures.

EXAMPLE 16

This example demonstrates the use of the invention methods to establish hormone secreting cells in culture from thyroid and pancreas tissue.

Sections of thyroid tumor were obtained from a 30 year old female donor. Sections of pancreatic tissue were obtained from the posterior lobe of the pancreas of an elderly female donor who was undergoing surgery because of an injury to the pancreas. Small chunks containing about 50 to 300 cells were teased apart from the tissue and placed in establishing culture medium as described in Example 13. The cultures were flooded with the medical gas mixture described supra every other day. After 2 weeks, the cultures were subdivided and placed in fresh establishing medium. Over the course of an additional 8 weeks in culture, the cell cultures were subdivided as needed, depending on the rate of cell proliferation.

After a total time in primary culture of 8 weeks (10 days synthesis time) the thyroid cells had accumulated thyroxine ($T_4$) in the medium at a concentration of 7.3 ug/Dl (assayed by a commercial clinical laboratory). This represents a considerable amount of thyroxine secretion when compared to the normal range for adult serum of 4 to 12 ug/Dl, and indicates that the thyroid cells were performing at least one differentiated thyroid function after 8 weeks in culture. The cells secreted no detectable amounts of progesterone or LH, but over 4 weeks of synthesis they accumulated estrogen in the amount of 255 pg/ml. The cells remained in follicle-like clusters throughout the culture period.

The pancreas cells proliferated in suspension in 15 ml DMSS (25 $cm^2$ Falcon flasks) during 8 weeks of primary, culture. Medium was collected for assay from the time spanning weeks 6 to 8 of culture (2 weeks synthesis time). As would be expected for cells of pancreatic origin, they did not secrete detectable amounts of progesterone, estrogen, or LH. Amylase and insulin concentrations were assayed by Sierra Nevada Labs, Reno, Nev. Amylase concentration in the medium was very low at 5 U/liter (normal range for human serum=34–122 U/liter). This indicated that there were very few cells of exocrine pancreas origin in the cultures. In contrast, the medium of most cultures contained greater than 400 IU/ml insulin, (normal range in a fasting individual=9.1–21.7 IU/ml). This indicated that the cultures contained β-cells of pancreatic endocrine islet origin, and that the cells actively secreted insulin into the medium. Individual cultures were selected for further propagation according to proliferation rate and amount of insulin secreted.

The pancreatic cells may be sub-cloned to produce cultures which produce human insulin and which are free of exocrine pancreatic cells.

Conclusion: The methods of this invention may be successfully applied to many cell types, including pancreatic insulin producing cells, in order to obtain useful cell cultures for diverse applications.

EXAMPLE 17

This examples demonstrates the maintenance of insulin-secreting cells in long-term culture, and the maintenance of the cells' insulin secretory capacity after freezing and thawing.

The pancreas cell cultures described in Example 16 were passaged approximately every 3–5 days through generation 47. Passaging was done by placing 0.5–1.0 ml of cell suspension into 10 ml fresh medium in a flask. Each flask was flooded with medical blood gas mixture (supra), sealed, and maintained in an incubator at 37° C. Typically, each flask was flooded with fresh gas every other day. At passage 47, the cells had been in continuous culture for 9.5 months.

A portion of the pancreas cells at generation 47 were frozen according to the method described in Example 15 using cryopreservative A. The cells were stored frozen for 1 day, after which they were thawed according to the method described in Example 15.

The thawed cells and cells from generation 47 which had not been frozen were placed in DMSS medium and centrifuged at 1070 rpm for 5 minutes. The pellets were washed and resuspended in 30 ml of Medium PDM (Dulbecco's salt solution, phosphate buffered, with $MgSO_4$ (no $MgCl_2$), plus 2% BSA Fraction V), final osmolality adjusted to 272 mOsm) at 37°.

The cells were incubated 30 minutes at 37°, then centrifuged and resuspended as above. Cell count and viability were determined by Trypan blue exclusion.

The cells were then centrifuged and resuspended in a base medium consisting of 3 parts Medium PDM (supra) and 1 part DMSS, as defined in Example 6 above. The cells were incubated for 1.5 or 3 hours in D(+)glucose at concentrations ranging from 1 to 21 mM as shown in Table 11 below. RIA analysis demonstrated that the cells responded to glucose by the secretion of insulin as shown in Table 11.

TABLE 11

| Glucose level | $\mu$IU insulin secreted/ml/ 10,000 cells | |
|---|---|---|
| total | pg 47 | pg47 frozen/thawed |
| 1 mM | 92 | 99 |
| 2 mM | 100 | 105 |
| 6 mM | 111 | 114 |
| 11 mM | 117 | 128 |
| 16 mM | 129 | 125 |
| 21 mM | 116 | 124 |

Conclusions: The pancreas cells were maintained in long term culture, during which time the cells maintained their capacity to secrete insulin in response to increased glucose concentrations. Moreover, cells which had been frozen and thawed retained their capacity for response to glucose, which response was comparable to that of non-frozen cells.

EXAMPLE 18

This example shows the time course of the human pancreas cells' response to glucose.

Human pancreas cell cultures from Example 16 were maintained in continuous culture through 55 generations, at which time they had been in culture for 12 months.

Two hours prior to the experiment, the cells were centrifuged at 1070 rpm for 5 minutes and then resuspended in glucose-poor medium consisting of 1 part DMSS plus 6 parts PDM. The cells were incubated in glucose-poor medium (glucose-starved) at a concentration of about 1.5× $10^6$ cells/ml in 10 ml culture flasks for two hours at 37°.

The cells were then centrifuged and resuspended in the experimental medium consisting of one part DMSS and six parts PDM. The glucose concentration in the experimental medium alone was 1.1 mM. To this medium was added glucose in the concentrations shown in Table 12 below, and the cells were incubated for various times. Samples were collected and assayed for insulin content as shown in Table 12.

TABLE 12

| MCC041291 | | 1,500,000 cells/ml | | 10 ml culture in flask | | |
|---|---|---|---|---|---|---|
| | | | | 5 hr | 7 hr | 24 hr |
| mM glucose added | 1 hr | 2 hr | 3 hr | $\mu$IU Insulin secreted/ 1.5 million cells/ml | | |
| 0 mM | 29 | 42 | 82 | 99 | 210 | 101 |
| 1 mM | 275 | 363 | 451 | 564 | 582 | 812 |
| 5.6 mM | 3413 | 982 | 999 | 2383 | 2718 | 2760 |
| 11.0 mM | 3376 | 1768 | 2220 | 1184 | 3202 | 1276 |
| 16.5 mM | 3716 | 2415 | 2450 | 2589 | 4039 | 2099 |
| 22 mM | 2538 | 1845 | 2066 | 1722 | 1320 | 989 |
| 33 mM | 972 | 345 | 446 | 657 | 1109 | 1073 |

Conclusions: The cells responded in graded dose-response fashion to increasing concentrations of glucose, with a maximal response at 16.5 mM, which is comparable to the response expected from normal human beta-cells in primary culture. The maximal response ranged from approximately 20 fold to 128 fold the basal level of insulin secretion.

EXAMPLE 19

This example shows that pancreas cells in continuous culture retain their capacity to secrete insulin in response to glucose.

A portion of the human pancreas cells from Example 16 at passage generation 21 were frozen according to the method described in Example 17, and then thawed 9.5 months later prior to the experiment. Passage generation 60 cells were maintained in continuous culture for 1 year. Both groups of cells were glucose-starved for 2 hours prior to the experiment, as described in Example 18. The cultures were then placed in 24 well plates at a concentration of $10^5$ cells/ml/well in an incubation medium of RPMI-1640-Y [100 ml glucose deficient RPMI-1640 (R 1383, Sigma), 1 gm BSA Fraction V, 1.5 ml HEPES solution, 5.5 ml tissue culture water, 1500 IU penicillin-G, 1.5 mg streptomycin, pH 7.4–7.6, final osmolarity adjusted to 272 mOsm].

The cells were incubated for 90 minutes or 5 hours in various concentrations of glucose as shown in FIG. 11.

Results: Cells which were frozen at passage 21 responded maximally to 11 mM and 16.5 mM glucose with an 8 to 9.5 fold increase in insulin secretion compared to control at 5 hours. Cells which had been maintained in continuous culture for 1 year (passage generation 60) responded to 5.6, 11, and 16.5 mM glucose with increases in insulin secretion ranging from 3 to 4.5 fold compared to control (FIG. 11).

EXAMPLE 20

This example demonstrates the response of pancreas cells in long-term culture to amino acids.

Human pancreas cells at passage generation 47, were prepared for the experiment as described in Example 17 above. The cells were incubated in 6 parts PDM plus 1 part DMSS medium at a concentration of $10^5$ cells/ml, at various concentrations of glucose. Alanine (10 mM) or arginine(20 mM) were added, and the cells were incubated for 90 minutes, at which time samples were collected for assay of insulin content. The results are shown in Table 13.

TABLE 13

Effect of amino acids on glucose stimulated insulin secretion

| total mM glucose | control | +10 mM alanine | +20 mM arginine |
|---|---|---|---|
| 1 mM | 91 | 103 | 128 |
| 2 mM | 108 | 135 | 134 |
| 6 mM | 112 | 127 | 105 |
| 11 mM | 116 | 117 | 93 |
| 16 mM | 128 | 101 | 99 |
| 22 mM | 115 | 87 | 94 |

Results: At low glucose concentrations (1, 2, and 6 mM), alanine increased insulin secretion beyond the level of glucose stimulation alone. The effect of alanine was most pronounced at 2 mM glucose, where alanine increased insulin secretion 1.25 fold over that stimulated by glucose alone. Arginine had a pronounced effect at 1 mM glucose, where arginine increased insulin secretion 1.4 fold over that stimulated by glucose alone.

EXAMPLE 21

This example demonstrates that human pancreas cells maintained in long term culture contain immunoreactive insulin.

Human pancreas cells from Example 16, passage generation 47, were fixed and permeabilized by −20° C. methanol, mounted, and stained by a standard immunochemical technique (Harlow, E. et al., 1988, *Antibodies: A Laboratory Manual,* Cold Spring Harbor Laboratories) using as a primary antibody an anti-human insulin antibody raised in guinea pig from Peninsula Laboratories, Belmont, Calif. The secondary antibody was anti-guinea pig IgG (whole molecule)—TRITC conjugate (Rb) from Sigma (T-7153). As a negative control, in place of the primary antibody, cells were incubated with the same primary anti-insulin antiserum which had been pre-incubated with synthetic human insulin to adsorb the anti-insulin antibodies. The cells were counterstained with Hoechst dye 33258. The immunostained cells were observed and photographed on a Zeiss IM35 microscope using a Zeiss #15 filter to illuminate the rhodamine dye labeling for insulin. The identical cell fields were observed and photographed using a Zeiss #2 filter to illuminate the Hoechst labeling of DNA in the nuclei of all cells in the field. Photographs of cell nuclei were compared with counterpart photographs of rhodamine labeled cell cytoplasms to determine how many cells in the field contained immunoreactive insulin.

Results: Controls showed no background staining. Comparison of numbers of labeled nuclei with numbers of cells immunoreactive to insulin revealed that greater than 60% of the cells in the culture contained immunoreactive insulin at different intensities of fluorescent staining.

EXAMPLE 22

This example demonstrates the production from human pancreas whole islets of daughter-islets containing immunoreactive insulin. The example demonstrates the long-term culturing of those islets.

Human pancreatic whole islets were isolated from cadaveric donor pancreases by collagenase digestion and purified by gradient centrifugation. A purity of about 40% was obtained. The isolation procedures were conducted as described in Soon-Shiong et al. (1994), "Insulin independence in a type 1 diabetic patient after encapsulated islet transplantation", *Lancet* 348:950–951. Whole islets are basement lamina (membrane) enclosed groups of pancreatic islet cells. The isolation procedure further comprised placing the whole islets into RPMI-1640 medium and shipping them at room temperature, overnight. The composition of RPMI-1640 obtained from Sigma, St. Louis, Mo. is set forth in Formula IV below. The RPMI-1640 medium was modified by adding fetal calf serum (final concentration 10%) and $ZnSO_4$—$7H_2O$ (final concentration 0.0008 gm/L). The final osmolality of the modified medium was about 290 to about 298. There were two shipments of units. The first shipment consisted of less than 100 whole islets at about a 40% purity, contained in a 15 ml "FALCON" test tube. The second shipment consisted of less than 80 whole islets at a purity of about 30% or less.

Formula IV

RPMI-1640

| Component | R8758 [1X] g/L |
|---|---|
| Inorganic Salts | |
| Calcium Nitrate-$4H_2O$ | 0.1 |
| Magnesium Sulfate (anhydrous) | 0.04884 |
| Potassium Chloride | 0.4 |
| Sodium Bicarbonate | 2.0 |
| Sodium Chloride | 6.0 |
| Sodium Phosphate Dibasic (anhydrous) | 0.8 |
| Amino Acids | |
| L-Arginine (free base) | 0.2 |
| L-Asparagine (anhydrous) | 0.05 |
| L-Aspartic Acid | 0.02 |
| L-Cystine-2HCl | 0.0652 |
| L-Glutamic Acid | 0.02 |
| L-Glutamine | 0.3 |
| Glycine | 0.01 |
| L-Histidine (free base) | 0.015 |
| Hydroxy L-Proline | 0.02 |
| L-Isoleucine | 0.05 |
| L-Leucine | 0.05 |
| L-Lysine HCl | 0.04 |
| L-Methionine | 0.015 |
| L-Pnenylalanine | 0.015 |
| L-Proline | 0.02 |
| L-Serine | 0.03 |
| L-Threonine | 0.02 |
| L-Tryptophan | 0.005 |
| L-Tyrosine 2Na-$2H_2O$ | 0.02883 |
| L-Valine | 0.02 |
| Vitamins | |
| D-Biotin | 0.0002 |
| Choline Chloride | 0.003 |
| Folic Acid | 0.001 |
| myo-Inositol | 0.035 |
| Niacinamide | 0.001 |
| p-Amino Benzoic Acid | 0.001 |
| D-Pantothenic Acid (hemicalcium) | 0.00025 |
| Pyridoxine-HCl | 0.001 |
| Riboflavin | 0.0002 |

-continued

| Component | R8758 [1X] g/L |
|---|---|
| Thiamine-HCI | 0.001 |
| Vitamin B-12 | 0.000005 |
| Other | |
| D-Glucose | 2.0 |
| Glutathione (reduced) | 0.001 |
| HEPES | — |
| Phenol Red-Na | 0.0053 |
| Specifications | |
| pH at RT (with sodium bicarbonate) | 7.3 ± 0.3 |
| Grams of powder required to prepare 1L | N/A |

Immediately after receipt of the shipment the whole islets were transferred at room temperature into "NUNCLON" culture dishes containing 8 ml of OCZEM-M media (Formula V, described below). Groups of about 8 to 10 whole islets were placed in each dish. The culture dishes were then placed into a glass desiccator at room temperature and gassed with the medical blood gas mixture (see Formula V). The lid was sealed and the desiccator was placed in a 37° C. $CO_2$ incubator overnight. The next day groups of 3 to 5 whole islets were transferred into fresh OCZEM-M medium in "NUNCLON" culture dishes at 37° C. The encapsulating basement lamina was breached in several places by using sterile glass microneedles with gentle manual microsurgery. Alternatively this breaching may be done through gentle application of collagenase to weaken the basement lamina, penetrating it in spots. This procedure was done in order to approximate the conditions that pertain during embryonic growth and the formation of the pancreas. In that instance, future islet cell proliferation is first preceded by a destabilization of the basement lamina at various sites followed by cell proliferation of islet cells at the destabilized sites.

Following the breaching of the basement membrane, the media (fresh OCZEM-M) was changed about every 3–5 days.

Formula V

OCZEM-M Media

| | gm/L |
|---|---|
| Inorganic Salts: | |
| Calcium Chloride.$2H_2O$ | 0.01604 |
| Calcium Nitride.$4H_2O$ | 0.03636 |
| Cupric Sulfate.$5H_2O$ | 0.0000009 |
| Ferrous Sulfate.$7H_2O$ | 0.0003032 |
| Magnesium Chloride | 0.04473 |
| Magnesium Sulfate (anhydrous) | 0.01776 |
| Potassium Chloride | 0.2269 |
| Sodium Bicarbonate | 1.1549 |
| Sodium Chloride | 4.7636 |
| Sodium Phosphate Dibasic (anhydrous) | 0.34256 |
| Zinc Sulfate.$7H_2O$ | 0.00663 |
| Vitamins: | |
| D-Biotin | 0.000073 |
| Choline Chloride | 0.00617 |
| Folic Acid | 0.00084 |
| p-Amino Benzoic Acid | 0.000091 |
| myo-Inositol | 0.05745 |

-continued

| | gm/L |
|---|---|
| Niacinamide | 0.00038 |
| D-Pantothenic Acid (hemicalcium) | 0.00018 |
| Pyridoxine.HCl | 0.00039 |
| Riboflavin | 0.00009 |
| Thiamine.HCl | 0.00049 |
| Vitamin $B_{12}$ | 0.0005 |
| (+) a-Tocopherol (Sigma T 1539) | 0.36 ml/L |
| Amino Acids: | |
| L-Alanine | 0.00327 |
| L-Arginine.HCl | 0.149 |
| L-Aspartic acid | 0.01211133 |
| L-Asparagine (anhydrous) | 0.02367 |
| L-Cysteine.2HCl | 0.03643 |
| L-Glutamic acid | 0.01262 |
| Glycine | 0.00637 |
| L-Histidine | 0.01308 |
| Hydroxy-L-Proline | 0.00727 |
| L-Isoleucine | 0.01961 |
| L-Leucine | 0.02294 |
| L-Lysine.HCl | 0.02782 |
| L-Methionine | 0.00708 |
| L-Phenylalanine | 0.00726 |
| L-Proline | 0.01982 |
| L-Serine | 0.01473 |
| L-Threonine | 0.01160 |
| L-Tryptophan | 0.00256 |
| L-Tryosine.2Na.$2H_2O$ | 0.01331 |
| L-Taurine | 0.09090 |
| L-Valine | 0.01153 |
| Other: | |
| Bovine Serum Albumin V (sigma A4949) | 1.818 |
| Ethylene Diaminetetraacetic Acid | 0.006 |
| D-Glucose | 1.3825 |
| L-Glutamine | 1.0618 |
| Glutathione, free acid (reduced) | 0.6549 |
| HEPES (N-2-Hydroxyethypiperazine-N'-2-ethanesulfonic acid) | 2.9788 |
| 2-Hydroxy-propyl-β-cyclodextrin | 0.1418 |
| Hypoxanthine | 0.00148 |
| L(+)-lactic acid:hemicalcium | 0.02909 |
| Linoleic Acid | 0.00003 |
| MOPS (3-[N-Morpholine]propane-sulfonic acid) | 2.093 |
| Putrescine.HCl | 0.00006 |
| Pyruvic Acid (sodium) | 0.28 |
| Thioctic Acid | 0.00007 |
| Thymidine | 0.00026 |
| Phenol Red (sodium) | 0.0 |
| SERU-MAX (Sigma 33765) | 94.55 ml/L |
| Synthetic serum substitute (Irvine Scientific Co. Cat. No. 99193) | 5.82 ml/L |

Final = 260 ± 1 mOSM
pH = 7.68, 37° C., when equilibrated with Medical Blood Gas (certified 5% oxygen, 5% carbon dioxide, 90% nitrogen. ± 0.1%)
Filtered 3X: 1st and 2nd 0.10 μm pore size (Nalgene Media - Plus 163-0010) 3rd 0.20 μm pore size (Nalgene syringe filter #190-2520)

Prior to preparing this media the 2-Hydroxy-propyl-β-cyclodextrin was added to "SERU-MAX" that had been thawed at 4° C. The "SERU-MAX"/dextrin mixture was then incubated at 2° C. overnight.

All steps were carried out under very dim light to guard against photoliability of any components. The medium was aliquoted into 40–50 ml batches equilibrated with the medical blood glass at 37° C. for 4 hrs. and then used immediately for culture.

The OCZEM-M media set forth in Formula V is specifically tailored for the long term culture of pancreatic islet cells. Listed below are several of the key media components, the preferred molarity of that component and also its acceptable molar range.

| Component | Actual Molarity | Molar Range |
|---|---|---|
| Zinc sulfate.7H$_2$O | 0.023 mM or (23.1 μM) | 0.0196 to 0.0265 |
| myo-Inositol | 0.3188 mM or (318.8 μM) | 0.271 to 0.367 |
| Niacinamide | 0.0311 mM or (31.1 μM) | 0.0264 to 0.0358 |
| L-Taurine | 0.7266 mM or (726.6 μM) | 0.617 to 0.870 |
| L-glutamine | 7.27 mM | 6.18 to 8.36 |
| Glutathione, free acid (reduced) | 2.131 mM | 1.70 to 2.56 |
| Pyruvic acid | 2.545 mM | 2.03 to 3.05 |
| EDTA | 20.5 μM or (0.0205 μM) | 0.016 to 0.025 |
| L(+)-lactic acid: hemicalcium | 0.266 mM or (266.6 μM) | 0.21 to 0.32 |
| (+) a-Tocopherol | ~200 IU per liter | 160 IU to 240 IU |

Although the OCZEM-M medium as set forth in Formula V and as listed above is used to culture pancreatic cells, the same medium with lower level zinc (ZnSO$_4$.7H$_2$O-0.0008 gm/L) makes an excellent long term cell culturing medium for other hormone secreting cells such as pituitary, thyroid and granulosa cells.

Photomicrographs were taken of the above-described microsurgically manipulated islets, immediately after the breach was made in the constraining basement lamina and on subsequent days in culture. This was done in order to monitor and document the subsequent series of events. Careful visual observations were also made. Initially a small nodule of a few islet cells appeared to protrude or develop through the breach in the basement lamina. Cell proliferation could be seen at the periphery of the nodule. Over a several week period the nodule grew in size and eventually pinched off from the original whole islet. This free nodule contained a small clump of islet cells unconstrained by a basement lamina. These small nodules, or "daughter islets", did not become attached to the bottom of the culture dish and could easily be picked up with a pipette for transfer to another culture dish. This allowed a selection against any fibroblasts that might grow out from the basement lamina constraint of the original whole islet. Fibroblasts have a dramatically different appearance and behavior in contrast to the islet cells. Fibroblasts are elongated, substrate attached to the bottom of the culture dish, grayish and have extended pseudopodia. Islet cells, in contrast, are round, not attached, or very loosely attached, but like to cluster together in small groups and have a healthy golden appearance when viewed with inverted phase optics at 160X to 400X.

The identification of the islet cells was made on the basis of (1) general morphological appearance, (2) immunohistological analysis of the presence of insulin within the cells, (3) the ability of the islet cells to secrete insulin in response to glucose stimulation, and (4) the presence of GABA (γ-amino butyric acid) in those cells. GABA is the principal inhibitory neurotransmitter in the brain and is a putative paracrine signal molecule in pancreatic islets. This enzyme is expressed only in the cytoplasm of GABA-secreting neurons and pancreatic B-cells thus showing a very restricted tissue distribution. (Solimena, M. et al. (1993), "Spotlight on a neuronal enzyme", *Nature* 366:15–16).

The materials and partial protocol used for the GABA determination were as follows:

1. Primary antibody: Rabbit anti-GABA (γ-amino butyric acid) Affinity Isolated Antibody [Sigma Chemical Co. A-2052] working dilution used was 1:10,000
2. Secondary antibody: Goad anti-rabbit IgG (whole molecule) Antibody (adsorbed with human IgG)—peroxidase labeled [Sigma A-0545] Working dilution used was 1:200.
3. Substrate system: 3,3'-Diaminobenzidine (DAB) [Sigma, Fast DAB set, D-4168] Used according to manufactures specified protocol.
4. Negative controls: The primary antibody was not added to the control slides.
5. Nuclear counterstain: Hoechst 33258 [Sigma Chemical Co.], 0.1% was used.

The procedures followed for fixing the islet cells and the amount of primary and secondary antibodies used are given in detail in the description for Example 23, infra. The appearance of the dark brown insoluble precipitate from the DAB substrate was scored in the cells as positive for GABA.

A total of four slides was used for the control and five for the anti-GABA antibody treated cells. Of the 157 Hoechst stained control cells that were screened, zero were positive for GABA. Of the 231 screened Hoechst stained cells treated with anti-GABA antibody, 184 were positive for GABA.

The occurrence of cell division was assessed by (1) careful microscopic observation with cell counts, (2) immuno-histochemical analysis of bromodeoxyuridine (BUDR or more recently BRUD) incorporation into the DNA of dividing cells (Example 23). In addition, cells that had undergone mitosis (as assayed by BUDR incorporation into their DNA) were also analyzed for the ability of that cell to synthesize insulin. Determination of insulin synthesis was accomplished by assaying for co-localization of BUDR incorporation and the presence of insulin within a single cell by immunohistochemical methods.

Cultures of the small daughter-islets were tested for their ability to exhibit glucose stimulated insulin synthesis by immunohistochemical analysis at two times during the culture period. The first assessment was made after three months in culture at the eighth passage generation and the second assessment was made after the sixteenth passage generation and eight months in continuous culture. On the average the daughter-islet cells were passed every 10–14 days. To test the response of the cells to glucose stimulation, the cultures were given a glucose poor basal medium. The basal medium as set forth in Formula VI below was a RPMI-1640 derivative containing 2 mM glucose. The cells remained in glucose poor medium for a period of 4 hours. The cells were first washed five times for 10 minutes each in the Formula VI medium prior to a 3 hour final incubation in the same basal medium. Subsequently the cultures were placed in the same medium, except that its total glucose concentration was 12 mM (instead of 2 mM glucose) for 3 hours and then prepared for indirect immunofluorescence to detect the presence of insulin.

Formula VI

RPMI-1640 Deficient Medium (without L-glutamine, Glucose or Sodium Bicarbonate)

| To that, was added the following: | gm/L |
|---|---|
| Zinc sulfate.7H$_2$O | 0.0066 |
| myo.Inositol | 0.0224 |
| Niacinamide | 0.0024 |
| L-Taurine | 0.090 |
| L-glutamine | 1.0618 |

-continued

| To that, was added the following: | gm/L |
|---|---|
| Glucose | 0.360 |
| Pyruvic acid (sodium) | 0.28 |
| EDTA (ethylenediamine tetraacetic acid) | 0.006 |
| Bovine Serum Album V (Sigma A4919) | 5.0 |
| Glutathione, free acid (reduced) | 0.654 |
| HEPES (N-2-Hydrozyethylpiper-Azine-N'-2-ethanesulfonic acid) free acid | 2.9788 |
| Sodium bicarbonate | 1.16 |

MOPS (30[N-Morpholino]propane-sulfonic acid) 2.09
mOsm=260
filtered 2x:1st & 2nd
0.10 μm pore size (Nalgene Media-Plus #163-0010)

The materials and partial protocol used in this example were as follows:
1. Primary antibody: Guinea pig monoclonal anti-insulin (human) [Peninsula Laboratories, Inc. IFK-7303G] working dilution used was 1:200.
2. Secondary antibody: Rabbit anti-guinea pig IgG (whole molecule) affinity isolated—TRITC conjugate (Sigma T-7153).
3. Negative control: 1 ml of the primary antiserum of the Guinea pig monoclonal anti-insulin (human) was added to 50 μgm of synthetic human insulin (Peninsula Laboratories, Inc.).
4. Nuclear counterstain: Hoechst 33258 (Sigma Chemical Co.), 0.1% was used.

The procedures followed for fixing the cells and the amount of primary and secondary antibodies used are given in detail in the description of procedures for Example 23. The control experiment was exposure only to the glucose poor basal medium. The results are shown in Table 14 below.

TABLE 14

| | Control | 3 mo. culture (8th passage generation) | 8 mo. culture (16th passage generation) |
|---|---|---|---|
| Total # cells screened (Hoechst) | 168 | 388 | 195 |
| # cells positive for insulin (anti-insulin-RITC) | -0- | 343 | 170 |
| % of insulin positive cells | -0- | 88% | 87% |

As shown in Table 14, the pseudo-islet cells produced insulin in response to 12 mM glucose stimulation. The percentage of cells exhibiting glucose stimulated insulin response remained the same at 8th passage generation (3 months of culture) and the 16th passage generation (8 months of cell culture).

EXAMPLE 23

This example determined the percent of cultured pancreatic islet cells that exhibits mitosis as assayed by incorporation of BUDR during DNA synthesis and also showed that cells that have undergone proliferation retain their ability to respond to glucose stimulation and synthesize insulin. The measurements were determined by indirect immunofluorescence assessment of colocalization of BUDR incorporation and insulin positive cytoplasm in a single cell.

The tests were done on the same long term cultured daughter-islets described in Example 22, after 3 months of culture (8 passage generations) and after 8 months of cell culture (16 passage generations). Cultures of the daughter-islets were exposed to 30 μgm/ml BUDR for 5 days. The cultures were then placed in normal culture medium (OCZEM-M) for another 5 days. Cultures were then given the same glucose poor basal medium described in Formula VI for 4 hours. Subsequently medium containing 12 mM glucose, described in Example 22, was provided for 6 hours. Cells were immediately fixed and prepared for immunofluorescence. A FITC conjugated secondary antibody to detect BUDR incorporation during DNA synthesis and a TRITC conjugated secondary antibody to detect insulin synthesis in response to glucose stimulation were used according to the following protocol.

Protocol a. Primary antibodies
  1. Mouse monoclonal anti-BUDR [Sigma B-2531]; working dilution used was 1:500
  2. Guinea Pig monoclonal anti-Insulin (Human) [Peninsula Laboratories, Inc. IFK-7303G]; working dilution used was 1:200.

b. Secondary antibodies
  1. Goat anti-Mouse IgG (FAB specific) adsorbed with Human IgG and Rat serum proteins—FITC conjugate [Sigma F-8771]
  2. Rabbit anti-Guinea pig IgG (whole molecule) affinity isolated—TRITC conjugate [Sigma T-7153]

c. Negative controls
  1. 1 ml primary antiserum of the Guinea pig monoclonal anti-insulin (human) was added to 50 ugm of synthetic human insulin.

d. Cell preparation used procedures to swell the nucleus and preferentially fix the chromosomes in order to maximize the ability to detect BUDR incorporation. The procedures are commonly used to prepare human embryonic cells for florescence in situ hybridization (FISH).
  1. Small groups of islet cells were put into hypnotic solution of 1% Na citrate in 6 mg BSA/ml for 5 minutes on a poly-lysine coated slide.
  2. Freshly prepared fixative of 3 parts Methanol: 1 part Acetic Acid was gently added and the cells allowed to fix at room temperature for 10 minutes.
  3. The cells were allowed to air dry with gentle air flow for 30 minutes then placed in Methanol at −20° C. overnight.
  4. The slides were slowly warmed to room temperature.
  5. 3 rinses (@6 minutes) with 0.1 M PBS were done.
  6. The slides were shaken 3–4 time to remove excess PBS.
  7. 100 ul of normal goat serum (1:10) and 50 ul of 6 mg BSA/ml were applied to each slide for 30 minutes, room temperature.
  8. Slides were rinsed 3 times with 0.1 M PBS and excess fluid blotted from the surrounding area.
  9. Primary antibodies were added, 100 ul @ and the slides were incubated in a moist chamber for 18 hours at 20° C.
    [100 ul of the premixed synthetic human insulin peptide+guinea pig anti-insulin were used instead of the primary antibody for human insulin in those slides to be used as negative controls for insulin synthesis.]
    [Negative controls for anti-BUDR were not as sophisticated and consisted of the deletion of the primary antibody: Mouse anti-BUDR.]

10. Slides were rinsed 3 times with 0.1 M PBS.
11. Secondary antibodies were added to EVERY slide (including the negative controls) in very dim light, 100 ul @ and then the slides were incubated in the dark for 60 minutes at room temperature.
12. Slides were rinsed gently 1 time with 0.1 M PBS for 10 minutes.
13. Hoechst 33258 (0.1%), 200 ul was added for 30 minutes.
14. Slides were rinsed 3 times with 0.1 M PBS.
15. Cover slip was mounted with Fluroguard (Cal BioChem).
16. After 24 hours the preparations were photographed with Kodak Ektar 100 using Zeiss optics and fluorescence filters (No 2 for Hoechst, No 9 for FITC and No 15 for TRITC).

The results are set forth below in Table 15.

TABLE 15

|  | 8th passage generation (3 mo. culture) | 16th passage generation (8 mos. culture) |
| --- | --- | --- |
| Total # cells analyzed (Hoechst) | 204 | 187 |
| Insulin positive | 175 | 168 |
| Insulin positive | 86% | 90% |
| BUDR incorporation | 89 | 80 |
| % BUDR incorporation | 44% | 43% |
| BUDR co-localization + insulin positive | 82 | 70 |
| % BUDR + insulin positive Total # BUDR | 92% | 87% |
| % of insulin -0- positive cells | 88% | 87% |

As shown in Table 15, approximately 43% of the pseudoislet cells underwent mitosis within a 10 day period. In the islet cell population that had recently undergone cell division a majority exhibited the ability to respond to a physiological level of glucose stimulation and produce insulin within the 10 day period of assessment. There were essentially no changes in those parameters when 3 month cell culture results were compared to the results obtained after 8 months of continuous culture. This Example shows that the characteristics of the daughter-islet cultures remained stable.

By the end of the three-month culture period, at a 43% rate of entry of the cells into the mitotic cycle within each 10-day period, there has been an increase of more than 20-fold in cell number in islet cells that have maintained their ability to produce insulin in response to 12 mM glucose.

EXAMPLE 24

Whole Islets in Culture

This example demonstrates the ability of human pancreas whole islets in culture to secrete insulin in response to glucose stimulation.

The whole islets were isolated and obtained as described in Example 22. Prior to this experiment they had been in culture for 3¾ months in OCZEM-M and were passage generation 11. Insulin secretion was measured by RIA (Diagnostic Products Corporation).

The cultured whole islets were washed in basal medium [RPMI (5x@ 20 minutes) before the experiment. Then individual whole islets were cultured in the basal level medium containing 2 mM glucose described in Example 22 for 3½ hours (1 islet/1 ml). Each individual islet was then transferred to 1 ml of the basal medium containing an additional 10 mM glucose (to yield a total glucose concentration of 12 mM) and cultured for another 3½ hours. A comparison of the resulting amounts of secreted insulin is shown below in Table 16. Each individual islet was placed in a separate culture dish after the experiment so that future tests on insulin secretion could be measured on identified islets.

TABLE 16

|  | Basal Medium (2 mM Glucose) | +10 mM Glucose (Total 12 mM Glucose) |
| --- | --- | --- |
|  | Secreted Insulin (uIU/ml/hr) | |
| Extra large islet (>250 $\mu$m) | 10.2 | 86.7 |
| Large islet (~150 $\mu$m) | 5.9 | 149.4 |
| 2 Medium islets @ (<1.5 $\mu$m) | 13.1 | 162.2 |
| 2 Very small islets @ (<0.5 $\mu$m) (together, they equaled less than 1 medium sized islet) | 3.9 | 84.5 |

As shown in Table 16, the ability of whole islets (human pancreatic) to respond to glucose stimulation and secrete insulin remains within physiological parameters after 3¾ months of culture. The amount of secreted insulin was approximately that observed for freshly isolated human whole islets. These results showed that there was no significant attenuation of response. These results also showed that the response to 12 mM glucose exposure elicits insulin secretion on the order of 7 to 26 times higher than the insulin secretion observed at the basal level of 2 mM glucose exposure.

EXAMPLE 25

Daughter-islets in Culture

This example demonstrates the ability of daughter-islet cells to secrete insulin in response to glucose stimulation. The daughter-islets were obtained as progeny arising through cell division from islet cells in the cultured whole islets obtained as isolates from human pancreases. After 17 months of culture the daughter-islet cells were analyzed for their ability to secrete insulin in response to physiological levels of glucose. Formula VI, as described in Examples 22 and 24 with designated glucose concentrations of 2 mM (Basal level), 7.6 mM (Maintence level), 12 mM and 22 mM was used for the experiment. Care was taken to control the osmolarity of each medium to the range of 260–268 mOsm so that no strong osmotic shock was administered to the daughter-islet cells. The cells were washed 5 times, at 20 minutes each wash, with the basal level medium (2 mM glucose level) before the experiment. Each group of 5 daughter-islet was placed in 1 ml of the test medium and incubated at 37° C., with 5% $CO_2$/5% $O_2$/90% $N_2$, for one hour. The medium was collected for assay and new medium containing 7.6 mM glucose was added. The one hour incubation, using the same conditions was then repeated. Those steps were repeated for the challenges with medium containing 12 mM and 22 mM glucose. Analysis of insulin secretion levels was done by RIA as described in Example 24.

TABLE 17

Daughter Islet Cell Insulin Secretion
Secreted Insulin ($\mu$IU/ml/hour/$10^3$ cells)

| Glucose Concentration | | | |
|---|---|---|---|
| 2 mM (Basal level) | 7.6 mM (Maintenance Level) | 12 mM | 22 mM |
| 0.30 | 25.1 | 38.6 | 144.5 |

As shown in Table 17, daughter-islet cells or progeny cells (produced through cell division of human pancreatic islet cells) prepared according to the method of the invention manifest the ability to respond to glucose stimulation and secrete insulin within physiological parameters after 17 months in culture. These islets cell cultures secreted about 1 $\mu$IU to about 150 $\mu$IU per milliliter per hour per thousand cells in a dose related response to administration of 3 mM up through 22 mM glucose. The maximal response was 482 times the basal level of 0.3 $\mu$UI/ml/hr/$10^3$ cells.

Such islet cell cultures may serve as a source of material for physiologically responsive human islet cells for construction of an artifical pancreas and implantation for clinical treatment of diabetes.

What is claimed is:

1. A method for establishing, maintaining and propagating a cell culture of gonadotrophin-secreting human pituitary tumor cells in vitro comprising the steps of:
    a) selecting at least one human pituitary tumor cell having gonadotrophin-secreting potential from a population of similar cells having gonadotrophin-secreting potential,
    b) placing said cell or cells in an establishing medium comprising:
        (i) a basal medium comprising essential minerals, salts, vitamins, amino acids, and lipids;
        (ii) a buffering system;
        (iii) glutamine in the amount of about 6.18 mM to about 8.36 mM;
        (iv) pyruvate;
        (v) niacinamide;
        (vi) myo-Inositol; and
        (vii) supplements of a fibroblast growth factor, an epidermal growth factor, insulin, ethanolamine, selenium, transferrin and hydrocortisone,
        said establishing medium promoting the viability and proliferation of said cell or cells for at least about 13 days in vitro, and
    c) maintaining the viability of at least one of said cells or the progeny of said cell for at least about 15 days in vitro wherein said viable cell secretes or viable cells secrete at least 4.04 mIU of follicle stimulating hormone (FSH)/ml establishing medium or at least 11.3 mIU of luteinizing hormone (LH)/ml establishing medium over a 10-day synthesis time in a substantially estrogen free culture.

2. A method for establishing, maintaining and propagating a cell culture of gonadotrophin-secreting human pituitary tumor cells in vitro comprising the steps of:
    a) selecting at least one human pituitary tumor cell having gonadotrophin-secreting potential from a population of similar cells having gonadotrophin-secreting potential,
    b) placing said cell or cells in an establishing medium comprising:
        (i) a basal medium comprising essential minerals, salts, vitamins, amino acids, and lipids;
        (ii) a buffering system;
        (iii) glutamine in the amount of about 6.18 mM to about 8.36 mM;
        (iv) pyruvate;
        (v) niacinamide;
        (vi) myo-Inositol; and
        (vii) supplements of a fibroblast growth factor, an epidermal growth factor, insulin, ethanolamine, selenium, transferrin and hydrocortisone,
        said establishing medium promoting the viability and proliferation of said cell or cells for at least about 13 days in vitro, and
    c) maintaining the viability of at least one of said cells or the progeny of said cell for at least about 15 days in vitro wherein said viable cell secretes or viable cells secrete at least 4.04 mIU FSH/ml establishing medium and at least 11.3 mIU LH/ml establishing medium over a 10 day synthesis time in a substantially estrogen free culture.

3. A method for establishing, maintaining and propagating a cell culture of gonadotrophin-secreting human pituitary tumor cells in vitro comprising the steps of:
    a) selecting at least one human pituitary tumor cell having gonadotrophin-secreting potential from a population of similar cells having gonadotrophin-secreting potential,
    b) placing said cell or cells in an establishing medium comprising:
        (i) a basal medium comprising essential minerals, salts, vitamins, amino acids, and lipids;
        (ii) a buffering system;
        (iii) glutamine in the amount of about 6.18 mM to about 8.36 m;
        (iv) pyruvate;
        (v) niacinamide;
        (vi) myo-Inositol; and
        (vii) supplements of a fibroblast growth factor, an epidermal growth factor, insulin, ethanolamine, selenium, transferrin and hydrocortisone,
        said establishing medium promoting the viability and proliferation of said cell or cells for at least about 13 days in vitro, and
    c) maintaining the viability of at least one of said cells or the progeny of said cell for 28 days in vitro wherein said viable cell secretes or viable cells secrete 3.0 mIU LH/ml establishing medium in a substantially estrogen free culture over 8 days.

* * * * *